United States Patent
An et al.

(10) Patent No.: US 10,463,305 B2
(45) Date of Patent: Nov. 5, 2019

(54) MULTI-DEVICE CARDIAC RESYNCHRONIZATION THERAPY WITH TIMING ENHANCEMENTS

(71) Applicant: CARDIAC PACEMAKERS, INC., St. Paul, MN (US)

(72) Inventors: Qi An, Blaine, MN (US); Pramodsingh Hirasingh Thakur, Woodbury, MN (US); Stephen J. Hahn, Shoreview, MN (US); Yinghong Yu, Shoreview, MN (US); Krzysztof Z. Siejko, Maple Grove, MN (US); Viktoria A. Averina, Shoreview, MN (US); Brendan Early Koop, Ham Lake, MN (US); Keith R. Maile, New Brighton, MN (US); Bin Mi, Plymouth, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 190 days.

(21) Appl. No.: 15/793,475

(22) Filed: Oct. 25, 2017

(65) Prior Publication Data
US 2018/0116593 A1   May 3, 2018

Related U.S. Application Data

(60) Provisional application No. 62/413,624, filed on Oct. 27, 2016.

(51) Int. Cl.
*A61N 1/368*   (2006.01)
*A61B 5/00*   (2006.01)
(Continued)

(52) U.S. Cl.
CPC ............ *A61B 5/686* (2013.01); *A61N 1/0587* (2013.01); *A61N 1/3627* (2013.01);
(Continued)

(58) Field of Classification Search
None
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)
(Continued)

*Primary Examiner* — Kennedy Schaetzle
(74) *Attorney, Agent, or Firm* — Seager, Tufte & Wickhem LLP

(57) ABSTRACT

Methods, systems and devices for providing cardiac resynchronization therapy (CRT) to a patient using a leadless cardiac pacemaker (LCP) and an extracardiac device (ED). The system is configured to identify atrial events to use as timing markers for the LCP to deliver CRT, and further to determine whether the timing markers are incorrectly sensed and to make adjustment or call for re-initialization as needed.

20 Claims, 25 Drawing Sheets

(51) Int. Cl.
    *A61N 1/362*     (2006.01)
    *A61N 1/05*     (2006.01)
    *A61B 5/0452*     (2006.01)
    *A61N 1/365*     (2006.01)
    *A61N 1/37*     (2006.01)
    *A61N 1/372*     (2006.01)

(52) U.S. Cl.
    CPC .......... *A61N 1/3684* (2013.01); *A61B 5/0452* (2013.01); *A61B 5/6869* (2013.01); *A61N 1/3622* (2013.01); *A61N 1/36514* (2013.01); *A61N 1/371* (2013.01); *A61N 1/37205* (2013.01)

(56) References Cited

U.S. PATENT DOCUMENTS

| | | | |
|---|---|---|---|
| 4,142,530 A | 3/1979 | Wittkampf | |
| 4,151,513 A | 4/1979 | Menken et al. | |
| 4,157,720 A | 6/1979 | Greatbatch | |
| RE30,366 E | 8/1980 | Rasor et al. | |
| 4,243,045 A | 1/1981 | Maas | |
| 4,250,884 A | 2/1981 | Hartlaub et al. | |
| 4,256,115 A | 3/1981 | Bilitch | |
| 4,263,919 A | 4/1981 | Levin | |
| 4,310,000 A | 1/1982 | Lindemans | |
| 4,312,354 A | 1/1982 | Walters | |
| 4,323,081 A | 4/1982 | Wiebusch | |
| 4,357,946 A | 11/1982 | Dutcher et al. | |
| 4,365,639 A | 12/1982 | Goldreyer | |
| 4,440,173 A | 4/1984 | Hudziak et al. | |
| 4,476,868 A | 10/1984 | Thompson | |
| 4,522,208 A | 6/1985 | Buffet | |
| 4,537,200 A | 8/1985 | Widrow | |
| 4,556,063 A | 12/1985 | Thompson et al. | |
| 4,562,841 A | 1/1986 | Brockway et al. | |
| 4,593,702 A | 6/1986 | Kepski et al. | |
| 4,593,955 A | 6/1986 | Leiber | |
| 4,630,611 A | 12/1986 | King | |
| 4,635,639 A | 1/1987 | Hakala et al. | |
| 4,674,508 A | 6/1987 | DeCote | |
| 4,712,554 A | 12/1987 | Garson | |
| 4,729,376 A | 3/1988 | DeCote | |
| 4,754,753 A | 7/1988 | King | |
| 4,759,366 A | 7/1988 | Callaghan | |
| 4,776,338 A | 10/1988 | Lekholm et al. | |
| 4,787,389 A | 11/1988 | Tarjan | |
| 4,793,353 A | 12/1988 | Borkan | |
| 4,819,662 A | 4/1989 | Heil et al. | |
| 4,858,610 A | 8/1989 | Callaghan et al. | |
| 4,886,064 A | 12/1989 | Strandberg | |
| 4,887,609 A | 12/1989 | Cole, Jr. | |
| 4,928,688 A | 5/1990 | Mower | |
| 4,967,746 A | 11/1990 | Vandegriff | |
| 4,987,897 A | 1/1991 | Funke | |
| 4,989,602 A | 2/1991 | Sholder et al. | |
| 5,012,806 A | 5/1991 | De Bellis | |
| 5,036,849 A | 8/1991 | Hauck et al. | |
| 5,040,534 A | 8/1991 | Mann et al. | |
| 5,058,581 A | 10/1991 | Silvian | |
| 5,078,134 A | 1/1992 | Heilman et al. | |
| 5,109,845 A | 5/1992 | Yuuchi et al. | |
| 5,113,859 A | 5/1992 | Funke | |
| 5,113,869 A | 5/1992 | Nappholz et al. | |
| 5,117,824 A * | 6/1992 | Keimel ................ | A61N 1/3704 607/14 |
| 5,127,401 A | 7/1992 | Grevious et al. | |
| 5,133,353 A | 7/1992 | Hauser | |
| 5,144,950 A | 9/1992 | Stoop et al. | |
| 5,170,784 A | 12/1992 | Ramon et al. | |
| 5,179,945 A | 1/1993 | Van Hofwegen et al. | |
| 5,193,539 A | 3/1993 | Schulman et al. | |
| 5,193,540 A | 3/1993 | Schulman et al. | |
| 5,241,961 A | 9/1993 | Henry | |
| 5,243,977 A | 9/1993 | Trabucco et al. | |
| 5,259,387 A | 11/1993 | dePinto | |
| 5,269,326 A | 12/1993 | Verrier | |
| 5,284,136 A | 2/1994 | Hauck et al. | |
| 5,300,107 A | 4/1994 | Stokes et al. | |
| 5,301,677 A | 4/1994 | Hsung | |
| 5,305,760 A | 4/1994 | McKown et al. | |
| 5,312,439 A | 5/1994 | Loeb | |
| 5,313,953 A | 5/1994 | Yomtov et al. | |
| 5,314,459 A | 5/1994 | Swanson et al. | |
| 5,318,597 A | 6/1994 | Hauck et al. | |
| 5,324,316 A | 6/1994 | Schulman et al. | |
| 5,331,966 A | 7/1994 | Bennett et al. | |
| 5,334,222 A | 8/1994 | Salo et al. | |
| 5,342,408 A | 8/1994 | deCoriolis et al. | |
| 5,370,667 A | 12/1994 | Alt | |
| 5,372,606 A | 12/1994 | Lang et al. | |
| 5,376,106 A | 12/1994 | Stahmann et al. | |
| 5,383,915 A | 1/1995 | Adams | |
| 5,388,578 A | 2/1995 | Yomtov et al. | |
| 5,404,877 A | 4/1995 | Nolan et al. | |
| 5,405,367 A | 4/1995 | Schulman et al. | |
| 5,411,031 A | 5/1995 | Yomtov | |
| 5,411,525 A | 5/1995 | Swanson et al. | |
| 5,411,535 A | 5/1995 | Fujii et al. | |
| 5,456,691 A | 10/1995 | Snell | |
| 5,458,622 A | 10/1995 | Alt | |
| 5,466,246 A | 11/1995 | Silvian | |
| 5,468,254 A | 11/1995 | Hahn et al. | |
| 5,472,453 A | 12/1995 | Alt | |
| 5,522,866 A | 6/1996 | Fernald | |
| 5,540,727 A | 7/1996 | Tockman et al. | |
| 5,545,186 A | 8/1996 | Olson et al. | |
| 5,545,202 A | 8/1996 | Dahl et al. | |
| 5,571,146 A | 11/1996 | Jones et al. | |
| 5,591,214 A | 1/1997 | Lu | |
| 5,620,466 A | 4/1997 | Haefner et al. | |
| 5,634,938 A | 6/1997 | Swanson et al. | |
| 5,649,968 A | 7/1997 | Alt et al. | |
| 5,662,688 A | 9/1997 | Haefner et al. | |
| 5,674,259 A | 10/1997 | Gray | |
| 5,683,426 A | 11/1997 | Greenhut et al. | |
| 5,683,432 A | 11/1997 | Goedeke et al. | |
| 5,702,427 A | 12/1997 | Ecker et al. | |
| 5,706,823 A | 1/1998 | Wodlinger | |
| 5,709,215 A | 1/1998 | Perttu et al. | |
| 5,720,770 A | 2/1998 | Nappholz et al. | |
| 5,728,154 A | 3/1998 | Crossett et al. | |
| 5,741,314 A | 4/1998 | Daly et al. | |
| 5,741,315 A | 4/1998 | Lee et al. | |
| 5,752,976 A | 5/1998 | Duffin et al. | |
| 5,752,977 A | 5/1998 | Grevious et al. | |
| 5,755,736 A | 5/1998 | Gillberg et al. | |
| 5,759,199 A | 6/1998 | Snell et al. | |
| 5,774,501 A | 6/1998 | Halpern et al. | |
| 5,792,195 A | 8/1998 | Carlson et al. | |
| 5,792,202 A | 8/1998 | Rueter | |
| 5,792,203 A | 8/1998 | Schroeppel | |
| 5,792,205 A | 8/1998 | Alt et al. | |
| 5,792,208 A | 8/1998 | Gray | |
| 5,814,089 A | 9/1998 | Stokes et al. | |
| 5,827,216 A | 10/1998 | Igo et al. | |
| 5,836,985 A | 11/1998 | Goyal et al. | |
| 5,836,987 A | 11/1998 | Baumann et al. | |
| 5,842,977 A | 12/1998 | Lesho et al. | |
| 5,855,593 A | 1/1999 | Olson et al. | |
| 5,873,894 A | 2/1999 | Vandegriff et al. | |
| 5,891,184 A | 4/1999 | Lee et al. | |
| 5,897,586 A | 4/1999 | Molina | |
| 5,899,876 A | 5/1999 | Flower | |
| 5,899,928 A | 5/1999 | Sholder et al. | |
| 5,919,214 A | 7/1999 | Ciciarelli et al. | |
| 5,935,078 A | 8/1999 | Feierbach | |
| 5,941,906 A | 8/1999 | Barreras, Sr. et al. | |
| 5,944,744 A | 8/1999 | Paul et al. | |
| 5,954,757 A | 9/1999 | Gray | |
| 5,978,713 A | 11/1999 | Prutchi et al. | |
| 5,991,660 A | 11/1999 | Goyal | |
| 5,991,661 A | 11/1999 | Park et al. | |
| 5,999,848 A | 12/1999 | Gord et al. | |

(56) References Cited

U.S. PATENT DOCUMENTS

| | | |
|---|---|---|
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,505,077 B1 | 1/2003 | Kast et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,575 B2 | 12/2006 | Ostroff et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |

(56) References Cited

U.S. PATENT DOCUMENTS

| | | |
|---|---|---|
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,189,204 B2 | 3/2007 | Ni et al. |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,376,458 B2 | 5/2008 | Palreddy et al. |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,477,935 B2 | 1/2009 | Palreddy et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,340 B2 | 8/2010 | Sanghera et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,809,441 B2 | 10/2010 | Kane et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hubinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |

(56) References Cited

U.S. PATENT DOCUMENTS

| | | |
|---|---|---|
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,079,959 B2 | 12/2011 | Sanghera et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,116,867 B2 | 2/2012 | Ostroff |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,157,813 B2 | 4/2012 | Ko et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,195,308 B2 | 6/2012 | Frank et al. |
| 8,200,341 B2 | 6/2012 | Sanghera et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,034 B2 | 12/2012 | Patangay et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,399 B2 | 7/2013 | Degroot et al. |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,483,843 B2 | 7/2013 | Sanghera et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,878 B2 | 10/2013 | Allavatam et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,626,310 B2 | 1/2014 | Barror et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 * | 6/2014 | Greenhut .......... A61N 1/37288 607/4 |

(56) References Cited

U.S. PATENT DOCUMENTS

| | | |
|---|---|---|
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,325 B2 | 11/2014 | Boling et al. |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,072,914 B2 | 7/2015 | Greenhut et al. |
| 9,079,035 B2 | 7/2015 | Sanghera et al. |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |

(56) References Cited

U.S. PATENT DOCUMENTS

| | | |
|---|---|---|
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0275522 A1 | 11/2008 | Dong et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | Brooke |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0264949 A1 | 10/2009 | Dong et al. |
| 2009/0266573 A1 | 10/2009 | Engmark et al. |
| 2009/0270937 A1 | 10/2009 | Yonce et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |

(56) References Cited

U.S. PATENT DOCUMENTS

| | | |
|---|---|---|
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0305646 A1 | 12/2010 | Schulte et al. |
| 2010/0312309 A1 | 12/2010 | Harding |
| 2010/0331905 A1 | 12/2010 | Li et al. |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0178567 A1 | 7/2011 | Pei et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0029335 A1 | 2/2012 | Sudam et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0030484 A1 | 1/2013 | Zhang et al. |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0245709 A1 | 9/2013 | Bohn et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0310890 A1 | 11/2013 | Sweeney |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |

(56) References Cited

U.S. PATENT DOCUMENTS

| | | |
|---|---|---|
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0163631 A1 | 6/2014 | Maskara et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207013 A1 | 7/2014 | Lian et al. |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222099 A1 | 8/2014 | Sweeney |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0236253 A1 | 8/2014 | Ghosh et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0032173 A1 | 1/2015 | Ghosh |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0142069 A1* | 5/2015 | Sambelashvili ..... A61N 1/3688 607/18 |
| 2015/0142070 A1 | 5/2015 | Sambelashvili |
| 2015/0157861 A1 | 6/2015 | Aghassian |
| 2015/0165199 A1 | 6/2015 | Karst et al. |
| 2015/0173655 A1 | 6/2015 | Demmer et al. |
| 2015/0182751 A1 | 7/2015 | Ghosh et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297902 A1 | 10/2015 | Stahmann et al. |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0360036 A1 | 12/2015 | Kane et al. |
| 2016/0007873 A1 | 1/2016 | Huelskamp et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0038742 A1 | 2/2016 | Stahmann et al. |
| 2016/0038749 A1 | 2/2016 | Maile et al. |
| 2016/0045131 A1 | 2/2016 | Siejko |
| 2016/0045132 A1 | 2/2016 | Siejko |
| 2016/0045136 A1 | 2/2016 | Siejko et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0144190 A1 | 5/2016 | Cao et al. |
| 2016/0151621 A1 | 6/2016 | Maile et al. |
| 2016/0175601 A1 | 6/2016 | Nabutovsky et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0271406 A1 | 9/2016 | Maile et al. |
| 2016/0277097 A1 | 9/2016 | Ludwig et al. |
| 2016/0296131 A1 | 10/2016 | An et al. |
| 2016/0317825 A1 | 11/2016 | Jacobson |
| 2016/0367823 A1 | 12/2016 | Cowan et al. |
| 2017/0014629 A1* | 1/2017 | Ghosh .................. A61B 5/0452 |
| 2017/0021159 A1 | 1/2017 | Reddy et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056665 A1 | 3/2017 | Kane et al. |
| 2017/0056666 A1 | 3/2017 | Kane et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2017/0156617 A1 | 6/2017 | Allavatam et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2017/0368360 A1 | 12/2017 | Hahn et al. |
| 2018/0008829 A1 | 1/2018 | An et al. |
| 2018/0008831 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0021584 A1 | 1/2018 | An et al. |
| 2018/0036527 A1 | 2/2018 | Reddy et al. |
| 2018/0056075 A1 | 3/2018 | Hahn et al. |
| 2018/0056079 A1 | 3/2018 | Hahn et al. |
| 2018/0078773 A1 | 3/2018 | Thakur et al. |
| 2018/0116593 A1 | 5/2018 | An et al. |

FOREIGN PATENT DOCUMENTS

| | | |
|---|---|---|
| AU | 2014203793 A1 | 7/2014 |
| CA | 1003904 A1 | 1/1977 |

(56) References Cited

FOREIGN PATENT DOCUMENTS

| | | |
|---|---|---|
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2399645 A1 | 12/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |
| WO | 2016118735 A1 | 7/2016 |
| WO | 2016126661 A1 | 8/2016 |

OTHER PUBLICATIONS

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Spickler et al., "Totally Self-Contained Intracardiac Pacemaker," Journal of Electrocardiology, vol. 3(3&4): 324-331, 1970.

Wegmüller, "Intra-Body Communication for Biomedical Sensor Networks," Diss. ETH, No. 17323, 1-173, 2007.

Seyedi et al., "A Survey on Intrabody Communications for Body Area Network Application," IEEE Transactions on Biomedical Engineering, vol. 60(8): 2067-2079, 2013.

International Search Report and Written Opinion dated Jan. 26, 2018 for International Application No. PCT/US2017/058297.

* cited by examiner

MULTI-DEVICE CARDIAC RESYNCHRONIZATION THERAPY WITH TIMING ENHANCEMENTS

CROSS REFERENCE TO RELATED APPLICATIONS

The present application claims the benefit of and priority to U.S. Provisional Patent Application Ser. No. 62/413,624, filed on Oct. 27, 2016, and titled MULTI-DEVICE CARDIAC RESYNCHRONIZATION THERAPY WITH TIMING ENHANCEMENTS, the disclosure of which is incorporated herein by reference.

BACKGROUND

Cardiac resynchronization therapy (CRT) modifies the electrical activation and contractions of the heart's chambers to enhance pumping efficiency. Benefits may include increased exercise capacity and reduced hospitalization and mortality. More particularly, CRT devices operate by affecting the timing of contraction of one or more cardiac chambers relative to one or more other cardiac chambers. For example, contractions of one or more of the ventricle(s) may be timed relative to contraction of the atria, or contractions of the left and right ventricles may be timed relative to one another.

A "fusion" beat occurs when multiple activation signals affect the same cardiac tissue at the same time. For example, electrical fusion between pacing of one ventricle with spontaneous activation of another ventricle (for example, paced left ventricular (LV) activation and intrinsic right ventricular (RV) activation) produces a fusion beat. The generation of fusion beats is a goal of CRT in many circumstances.

Prior systems generally include intracardiac electrodes coupled via transvenous leads to an implanted pulse generator. The leads of such systems are widely known as introducing various morbidities and are prone to eventual conductor and/or insulator failure. Such issues likely reduce usage of CRT within the indicated population of heart failure patients.

Such prior lead systems typically include ventricular and atrial components to facilitate sensing of atrial and ventricular events to enhance CRT timing. For example, in some patients, CRT may be achieved by pacing the left ventricle at a specific time relative to detection of an atrial event. The atrial signal may conduct to the right ventricle (RV) via natural conduction to generate an RV contraction, with paced LV contraction occurring at a desirable time relative to the RV contraction to yield a fusion beat. The interval from the atrial sensed event to the LV pace may be adjusted to enhance cardiac response in prior systems.

Newer generation pacemakers include the leadless cardiac pacemaker (LCP), which can be implanted entirely within the heart and does not require a transvenous (or any) lead. Such devices are commercially available on a limited basis, but are currently indicated for and capable of use in only bradycardia pacing. With further enhancements, the LCP also presents an opportunity to provide an alternative to traditional CRT using transvenous leads. New and alternative systems, devices and methods directed at providing CRT using the LCP are desired.

OVERVIEW

The present inventors have recognized, among other things, that a problem to be solved is that the absence of an intracardiac lead makes detection of an atrial event for purposes of CRT potentially difficult for a system using one or more ventricular LCP devices. A second implantable device, such as a subcutaneous cardiac monitor (SCM), a subcutaneous implantable cardiac defibrillator (SICD), or a substernal variant of the SICD, may be used to assist in the timing of delivery of LCP CRT pacing. Such a second device may in some examples be referred to as an extracardiac device. There are various ways the second device can assist with achieved desired timing of the CRT, but each has shortcomings. The present inventors have identified new and/or alternative approaches to determining whether CRT in such a system is being provided appropriately and making adjustments to enhance CRT efficacy.

A first non-limiting example takes the form of an implantable medical device (IMD) system comprising: a leadless cardiac pacemaker (LCP) having a plurality of LCP electrodes, pacing circuitry configured to issue cardiac pacing outputs via the plurality of LCP electrodes, LCP communication circuitry configured to communicate to a second device, and operational circuitry configured to control the pacing circuitry to generate cardiac resynchronization therapy (CRT) using data received with the communication circuitry, the LCP further comprising a sensing input circuit to receive one or more biological signals to determine whether the CRT is achieving a desired result; an extracardiac device (ED) comprising: a plurality of electrodes for sensing cardiac signals; ED communication circuitry configured to communicate with at least the LCP communication circuitry; and ED operational circuitry configured to receive sensed cardiac signals from the plurality of electrodes and analyze cardiac activity. In this first illustrative non-limiting example, the ED operational circuitry is configured to obtain a cardiac signal from the plurality of electrodes, identify occurrence of a P-wave in the cardiac signal using a set of P-wave detection parameters, and use the ED communication circuitry to communicate to the LCP timing information related to the P-wave to assist in the CRT, such that the ED serves as a second device for purposes of the LCP communication circuitry, and the ED and LCP are configured to cooperatively adjust the P-wave detection parameters.

A second non-limiting example takes the form of an IMD system as in the first non-limiting example, wherein the ED and LCP are configured to cooperatively adjust the P-wave detection parameters by: at a first time including at least a first cardiac cycle: the ED detecting a P-wave using first P-wave detection parameters and using the ED communication circuitry to communicate to the LCP first timing information related to the detected P-wave; the LCP using the first timing information to deliver one or more CRT pacing therapies; the LCP determining that a delivered CRT pacing therapy has failed to achieve the desired result; and the LCP communicating the failure to achieve the desired result to the ED. Further in the second non-limiting example, in response to the LCP communicating failure to achieve the desired result, the ED adjusts the P-wave detection parameters to second P-wave detection parameters. Still further in the second non-limiting example, at a second time following the first time, the second time including at least a second cardiac cycle: the ED detecting a P-wave using second P-wave detection parameters and using the ED communication circuitry to communicate to the LCP second timing information related to the detected P-wave; and the LCP using the second timing information to deliver one or more CRT pacing therapies.

A third non-limiting example takes the form of an implantable medical device (IMD) system comprising: a leadless cardiac pacemaker (LCP) for delivering cardiac resynchronization therapy (CRT), the LCP comprising: a plurality of electrodes for delivering pacing therapy; a sensing input circuit to receive one or more biological signals; a pacing output circuit; LCP communication circuitry; and LCP operational circuitry configured to receive and analyze signals from the sensing input. The IMD system of this third non-limiting example also includes an extracardiac device (ED) comprising: a plurality of electrodes for sensing cardiac signals; ED communication circuitry configured to communicating with at least the LCP communication circuit; and ED operational circuitry configured to receive sensed cardiac signals from the plurality of electrodes and analyze cardiac activity. Further in the third non-limiting example, the ED operational circuitry is configured to obtain a cardiac signal from the plurality of electrodes, identify occurrence of a P-wave in the cardiac signal, and use the ED communication circuitry to communicate to the LCP that the P-wave has been detected; and the LCP operational circuitry is configured to determine from its analysis of signals received from the sensing input whether the ED is incorrectly detecting the P-wave.

A fourth non-limiting example takes the form of an implantable medical device (IMD) system comprising: a leadless cardiac pacemaker (LCP) for delivering cardiac resynchronization therapy (CRT), the LCP comprising: a plurality of electrodes for delivering pacing therapy; a sensing input circuit to receive one or more biological signals; a pacing output circuit; LCP communication circuitry; and LCP operational circuitry configured to receive and analyze signals from the sensing input. The system of the fourth non-limiting example further comprises an extracardiac device (ED) comprising: a plurality of electrodes for sensing cardiac signals; ED communication circuitry configured to communicating with at least the LCP communication circuit; and ED operational circuitry configured to receive sensed cardiac signals from the plurality of electrodes and analyze cardiac activity. Further in the system of the fourth non-limiting example, the ED operational circuitry is configured to obtain a cardiac signal from the plurality of electrodes, identify occurrence of a P-wave in the cardiac signal, and use the ED communication circuitry to communicate to the LCP that the P-wave has been detected; wherein the LCP operational circuitry is configured to use the pacing output circuit to deliver pace therapy and to use the sensing input circuit to determine whether a cardiac response to the pace therapy matches a desired metric; and the LCP operational circuitry is configured to communicate to the ED operational circuitry to indicate that the pace therapy does not match the desired metric.

A fifth non-limiting example takes the form of an implantable medical device (IMD) system comprising: a leadless cardiac pacemaker (LCP) having a plurality of LCP electrodes, pacing circuitry configured to issue cardiac pacing outputs via the plurality of LCP electrodes, LCP communication circuitry configured to communicate to a second device, and operational circuitry configured to control the pacing circuitry to generate cardiac resynchronization therapy (CRT) using data received with the communication circuitry, the LCP further comprising a sensing input circuit to receive one or more biological signals to determine whether the CRT is achieving a desired result. The fifth non-limiting example further includes an extracardiac device (ED) comprising: a plurality of electrodes for sensing cardiac signals; ED communication circuitry configured to communicating with at least the LCP communication circuitry; and ED operational circuitry configured to receive sensed cardiac signals from the plurality of electrodes and analyze cardiac activity. Further in the fifth non-limiting example, the ED operational circuitry is configured to obtain a cardiac signal from the plurality of electrodes, identify occurrence of a P-wave in the cardiac signal, and use the ED communication circuitry to communicate to the LCP timing information related to the P-wave to assist in the CRT; and the LCP operational circuitry is configured to communicate to the ED operational circuitry to indicate whether the CRT is achieving the desired result.

Additionally or alternatively, the ED may be configured to detect a P-wave by comparison of a cardiac electrical signal to a template to identify a match to the template, further wherein the ED may be configured to adjust the P-wave detection parameters by adjusting a match criteria.

Additionally or alternatively, the ED may be configured to detect a P-wave by comparison of a cardiac electrical signal to a template to identify a match to the template, further wherein the ED may be configured to adjust the P-wave detection parameters by changing the template.

Additionally or alternatively, the ED may be configured to detect a P-wave by identifying a peak among a set of peaks in a set of P-wave indicia; further wherein the ED may be configured to adjust the P-wave detection parameters by storing a parameter for selecting an Nth peak of the set of peaks.

Additionally or alternatively, the ED may be configured to detect a P-wave by comparing a set of P-wave indicia to a P-wave detection threshold; further wherein the ED may be configured to adjust the P-wave detection parameters by adjusting the P-wave detection threshold.

Additionally or alternatively, the P-wave indicia may comprise a series of samples of cardiac electrical data, or may comprise a series of correlation results generated by comparing a P-wave template to a cardiac electrical signal at a series of points in time.

Additionally or alternatively, the ED may be configured to detect a P-wave using a tracking analysis to track P-wave detections among a set of P-wave data captured for a series of cardiac cycles; further wherein the ED may be configured to adjust the P-wave detection parameters by adjusting the tracking analysis.

Additionally or alternatively, the LCP operational circuitry may be configured to determine whether the CRT is achieving a desired result and to communicate to the ED operational circuitry to indicate whether the CRT is achieving the desired result, wherein the ED and LCP are configured to cooperatively adjust the P-wave detection parameters in response to the LCP determining that the CRT is not achieving the desired result.

Additionally or alternatively, the LCP operational circuitry may be configured to determine whether the CRT is achieving a desired result by: storing one or more templates for a physiological signal sensed by the sensing input circuit, at least one of the templates representing the physiological signal corresponding to a preferred pace timing; and determining whether a test physiological signal captured in relation to a CRT pace therapy matches the template representing the physiological signal corresponding to the preferred pace timing. Additionally or alternatively, the one or more templates may comprise at least one offset template each representing the physiological signal corresponding to a known offset from the preferred pace timing; and the LCP may be configured to determine whether the test physiological signal matches one of the at least one offset templates and, if so, to communicate to the ED that an offset template match has occurred.

Additionally or alternatively, the ED may be configured, in response to the LCP communicating that an offset template match has occurred, to analyze the cardiac signal to determine whether a P-wave may have occurred at an offset relative to the detected P-wave, and, if so, making an adjustment to P-wave detection criteria.

Additionally or alternatively, the ED may be configured, in response to the LCP communicating that an offset template match has occurred, to reanalyze the cardiac signal to determine whether one or more adjustments to a P-wave detection criteria would result in detection of a P-wave correlated to the offset of the offset template that matched the test physiological signal.

Additionally or alternatively, the ED may be configured, in response to the LCP communicating that an offset template match has occurred, to make an adjustment to P-wave detection criteria using the offset.

Additionally or alternatively, if the test physiological signal does not match any of the one or more templates, the LCP may be configured to communicate that no template match occurred to the ED and further wherein, if the LCP finds at least a threshold quantity of test physiological signals fail to match any of the one or more templates, the IMD system may be configured to perform a re-initialization of one or more CRT system settings.

Additionally or alternatively, the one or more templates may include different templates for each of a plurality of system contexts. Additionally or alternatively, the plurality of system contexts may define a context for each of a plurality of cardiac rate zones. Additionally or alternatively, the plurality of system contexts may define a context for each of a plurality of postures, and at least one of the ED or the LCP may comprise a sensor to determine posture.

Additionally or alternatively, the LCP sensing input circuit to receive one or more biological signals may comprise a heart sound detector, and the one or more templates may include templates of heart sound signals. Additionally or alternatively, the LCP sensing input circuit to receive one or more biological signals may comprise a cardiac electrogram sensor, and the one or more templates may include templates of QRS morphology. Additionally or alternatively, the LCP sensing input circuit to receive one or more biological signals may comprise a pressure detector, and the one or more templates may include templates of pressure waveforms. Additionally or alternatively, the LCP sensing input circuit to receive one or more biological signals may comprise a motion detector, and the one or more templates may include templates of motion detector outputs over time. Additionally or alternatively, the LCP sensing input circuit to receive one or more biological signals may comprise an impedance measuring circuit, and the one or more templates may include templates of impedance changes over time. Additionally or alternatively the LCP sensing input circuit to receive one or more biological signals may comprise an optical sensor, and the one or more templates may include templates of optical sensor output over time.

Additionally or alternatively, the LCP may be configured to deliver CRT pacing output in response to communication of timing information related to the P-wave from the ED.

Additionally or alternatively, the LCP may be configured to deliver CRT pacing output according to a calculated interval relative to a prior CRT pacing output, such that the LCP is configured to use the communication of timing information related to the P-wave to adjust the calculated interval.

Additional embodiments may take the form of methods of providing CRT to a patient using any of these above non-limiting examples. In some such methods, an LCP may deliver the CRT pacing and observe a response to the pacing to determine whether desirable CRT results are occurring, and acts cooperatively with an ED in order to correct pace timing in the event that the desirable CRT results are not occurring.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following description should be read with reference to the drawings. The description and the drawings, which are not necessarily to scale, depict illustrative embodiments and are not intended to limit the scope of the disclosure.

Figure 1:
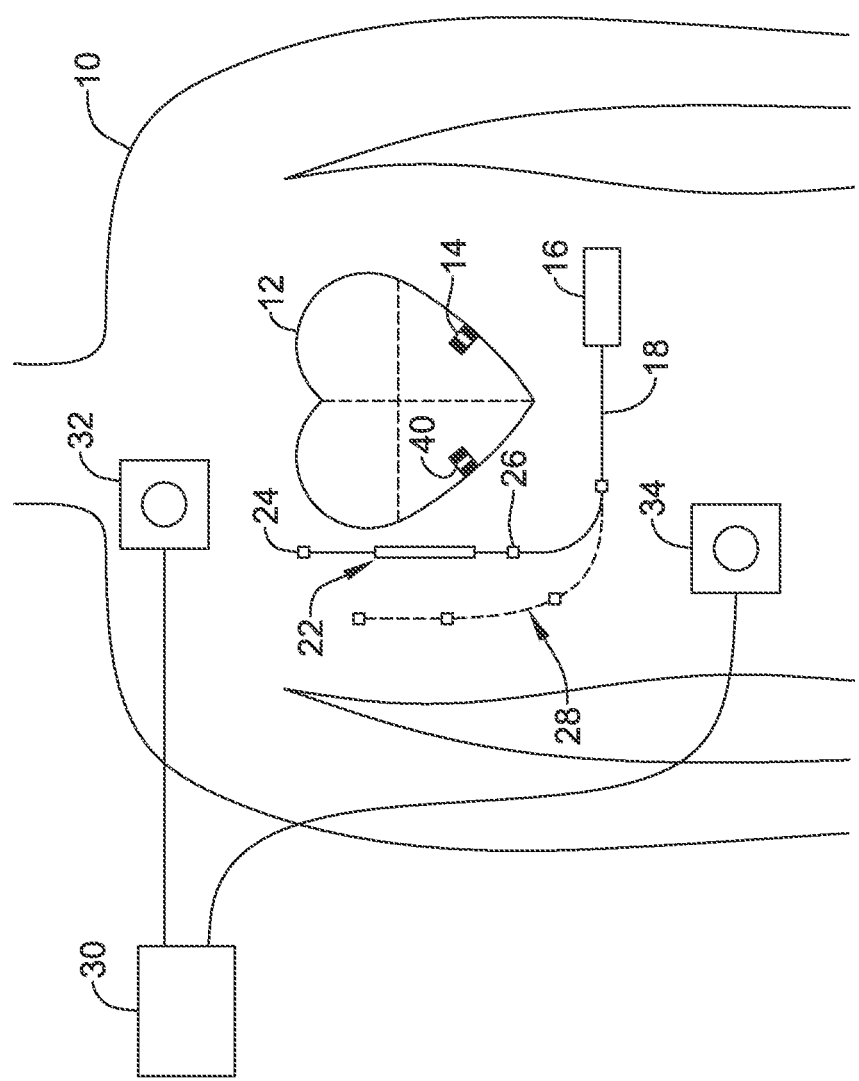
FIG. 1 illustrates a patient having a plurality of implantable medical devices.

FIG. 1 illustrates a patient 10 with a first implanted medical device, shown as a leadless cardiac pacemaker (LCP) 14 implanted inside the heart 12, in the left ventricle for illustrative purposes. The LCP 14 may be implanted in other chambers, such as the right ventricle or in the atrium, and more than one LCP may be provided.

A second medical device in the form of a subcutaneous implantable defibrillator (SICD) having a left axillary canister 16 and a lead 18 is also present. The illustrative lead 18 is shown with a defibrillation coil 22 and sensing electrodes 24, 26 distal and proximal of the coil 22. The lead 18 may optionally include a bifurcation 28 to provide an additional set of sensing or stimulus providing electrodes, if desired.

In some embodiments the lead may be as shown, for example, in U.S. Pat. No. 9,079,035, titled ELECTRODE SPACING IN A SUBCUTANEOUS IMPLANTABLE CARDIAC STIMULUS DEVICE, the disclosure of which is incorporated herein by reference. Rather than bifurcation, plural leads may be provided as shown, for example, in U.S. Pat. No. 7,149,575, titled SUBCUTANEOUS CARDIAC STIMULATOR DEVICE HAVING AN ANTERIORLY POSITIONED ELECTRODE. Any suitable design for single, multiple, or bifurcated implantable leads may be used.

The lead 18 may be implanted entirely subcutaneously, such as by extending across the anterior or posterior of the chest, or by going partly across the chest in a lateral/medial direction and then superiorly toward the head along the sternum. Some examples and discussion of subcutaneous lead implantation may be found in U.S. Pat. No. 8,157,813, titled APPARATUS AND METHOD FOR SUBCUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference.

A substernal placement may be used instead, with one finger 18/20 or the entire distal end of the lead (that is, the end distant from the canister 16) going beneath the sternum. Some examples of such placement are described in US PG Patent Pub. No. 2017/0021159, titled SUBSTERNAL PLACEMENT OF A PACING OR DEFIBRILLATING ELECTRODE, the disclosure of which is incorporated herein by reference. Still another alternative placement is shown in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

The devices 14 and 16 may communicate with one another and/or with an external programmer 30 using conducted communication, in some examples. Conducted communication is communication via electrical signals which propagate via patient tissue and are generated by more or less ordinary electrodes. By using the existing electrodes of the implantable devices, conducted communication does not rely on an antenna and an oscillator/resonant circuit having a tuned center frequency or frequencies common to both transmitter and receiver. RF or inductive communication may be used instead. Alternatively the devices 14 and 16 may communicate via inductive, optical, sonic, or RF communication, or any other suitable medium.

The programmer 30 may optionally use a wand (not shown) and/or skin electrodes 32 and 34 to facilitate communication. For example, skin electrodes 32 and 34 may be used for conducted communication with an implantable device. For other communication approaches such as RF or inductive communication, the programmer 30 may use a programming wand or may have an antenna integral with the programmer 30 housing for communication. Though not shown in detail, the programmer 30 may include any suitable user interface, including a screen, buttons, keyboard, touchscreen, speakers, and various other features widely known in the art.

Subcutaneous implantable defibrillators may include, for example, the Emblem S-ICD System™ offered by Boston Scientific Corporation. Combinations of subcutaneous defibrillators and LCP devices are discussed, for example, in US PG Patent Publication Nos. 20160059025, 20160059024, 20160059022, 20160059007, 20160038742, 20150297902, 20150196769, 20150196758, 20150196757, and 20150196756, the disclosures of which are incorporated herein by reference. The subcutaneous defibrillator and LCP may, for example, exchange data related to cardiac function or device status, and may operate together as a system to ensure appropriate determination of cardiac condition (such as whether or not a ventricular tachyarrhythmia is occurring), as well as to coordinate therapy such as by having the LCP deliver antitachycardia pacing in an attempt to convert certain arrhythmias before the subcutaneous defibrillator delivers a defibrillation shock. In addition, the two systems may coordinate as set forth herein to provide cardiac resynchronization therapy (CRT).

In some examples, rather than a therapy device such as the SICD shown in FIG. 1, a second implantable medical device may take the form of an implantable monitoring device such as a subcutaneous cardiac monitor (SCM). An SCM may be, for example, a loop monitor that captures data under select conditions using two or more sensing electrodes on a housing thereof and/or attached thereto with a lead. Such monitors have found use to assist in diagnosing cardiac conditions that may be infrequent or intermittent, or which have non-specific symptoms. In the context of the present invention, an SCM, or even a wearable cardiac monitor, may be used in place of the SICD as described in any of the following examples.

Several examples focus on using a left ventricular LCP 14. However, some examples may instead use a right ventricular LCP 40, and other examples may include both the left ventricular LCP 14 and right ventricular LCP 40. In other examples, a three implant system may include two LCP devices 14, 40, as well as a subcutaneous device such as the SICD 16. In still other examples, an atrial-placed LCP (not shown) may also be included or may take the place of one of the ventricular LCP devices 14, 40.

Figure 2:
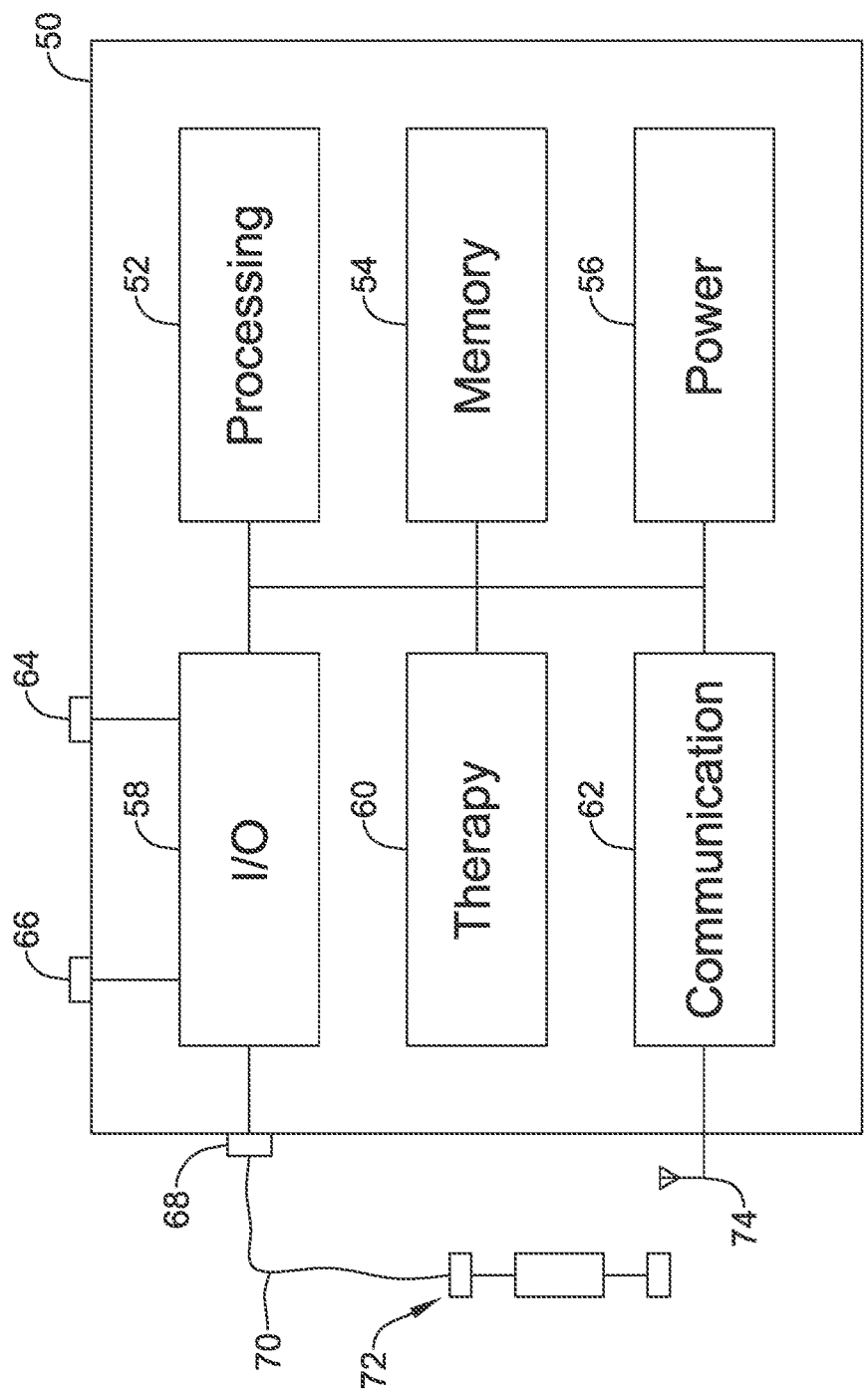
FIG. 2 shows an illustrative implantable medical device.

FIG. 2 illustrates a block diagram of an implantable medical device. The illustration indicates various functional blocks within a device 50, including a processing block 52, memory 54, power supply 56, input/output circuitry 58, therapy circuitry 60, and communication circuitry 62. These functional blocks make up the operational circuitry of the device. The I/O circuitry 58 can be coupled to one or more electrodes 64, 66 on the housing of the device 50, and may also couple to a header 68 for attachment to one or more leads 70 having additional electrodes 72.

The processing block 52 will generally control operations in the device 50 and may include a microprocessor or microcontroller and/or other circuitry and logic suitable to its purpose. A state machine may be included. Processing block 52 may include dedicated circuits or logic for device functions such as converting analog signals to digital data, processing digital signals, detecting events in a biological signal, etc. The memory block may include RAM, ROM, flash and/or other memory circuits for storing device parameters, programming code, and data related to the use, status, and history of the device 50. The power supply 56 typically includes one to several batteries, which may or may not be rechargeable depending on the device 50. For rechargeable systems there would additionally be charging circuitry for the battery (not shown).

The I/O circuitry 58 may include various switches or multiplexors for selecting inputs and outputs for use. I/O circuitry 58 may also include filtering circuitry and amplifiers for pre-processing input signals. In some applications the I/O circuitry will include an H-Bridge to facilitate high power outputs, though other circuit designs may also be used. Therapy block 60 may include capacitors and charging circuits, modulators, and frequency generators for providing electrical outputs. A monitoring device may omit the therapy block 60 and may have a simplified I/O circuitry used simply to capture electrical or other signals such as chemical or motion signals.

The communication circuitry 62 may be coupled to an antenna 74 for radio communication (such as Medradio, ISM, Bluetooth, or other RF), or alternatively to a coil for inductive communication, and/or may couple via the I/O circuitry 58 to a combination of electrodes 64, 66, 72, for conducted communication. Communication circuitry 62 may include a frequency generator/oscillator and mixer for creating output signals to transmit via the antenna 74. Some devices 50 may include a separate or even off-the shelf ASIC for the communications circuitry 62, for example. For devices using an inductive communication output, an inductive coil may be included. Devices may use optical or acoustic communication, and suitable circuits, transducers, generators and receivers may be included for these modes of communication as well or instead of those discussed above.

As those skilled in the art will understand, additional circuits may be provided beyond those shown in FIG. 2. For example, some devices 50 may include a Reed switch, Hall Effect device, or other magnetically reactive element to facilitate magnet wakeup, reset, or therapy inhibition of the device by a user, or to enable an MRI protection mode. A device lacking a lead may have plural electrodes on the housing thereof, as indicated at 64, 66, but may omit the header 68 for coupling to lead 70. In one example, a leadless device may use a header to couple to an electrode support feature that is attached to or wraps around the device housing.

Figure 3:
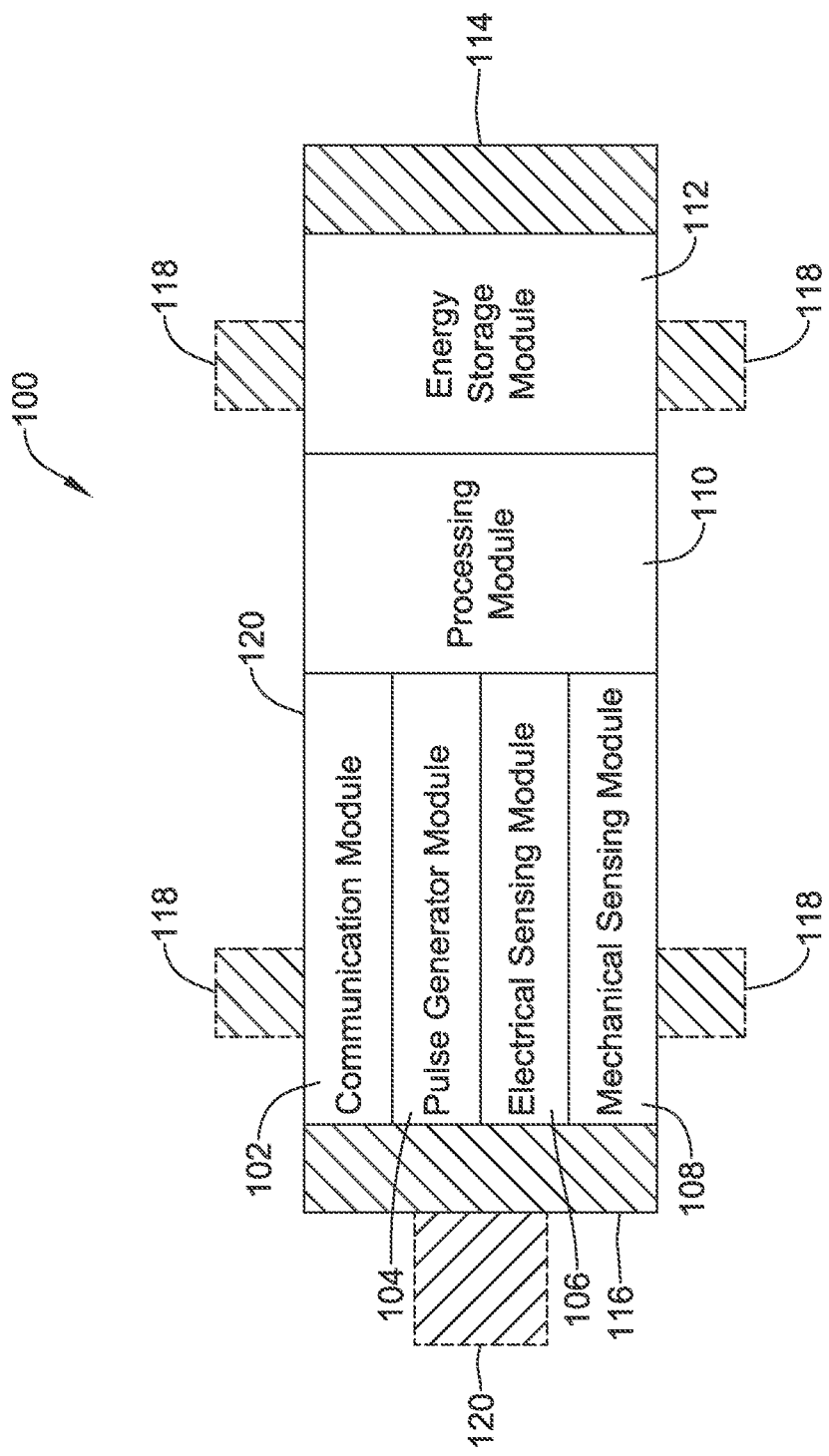
FIG. 3 shows an illustrative implantable leadless cardiac pacemaker.

FIG. 3 shows an illustrative LCP design. The LCP 100 is shown as including several functional blocks including a communications module 102, a pulse generator module 104, an electrical sensing module 106, and a mechanical sensing module 108. In some examples, the electrical sensing module 106 and mechanical sensing module 108 may be configured to sense a biological signal for use in assessing CRT efficacy.

A processing module 110 may receive data from and generate commands for outputs by the other modules 102, 104, 106, 108. An energy storage module is highlighted at 112 and may take the form of a rechargeable or non-rechargeable battery, or a supercapacitor, or any other suitable element. Various details of the internal circuitry, which may include a microprocessor or a state-machine architecture, are further discussed in US PG Patent Publications 20150360036, titled SYSTEMS AND METHODS FOR RATE RESPONSIVE PACING WITH A LEADLESS CARDIAC PACEMAKER, 20150224320, titled MULTI-CHAMBER LEADLESS PACEMAKER SYSTEM WITH INTER-DEVICE COMMUNICATION, 20160089539, titled REFRACTORY AND BLANKING INTERVALS IN THE CONTEXT OF MULTI-SITE LEFT VENTRICULAR PACING, and 20160059025, titled, MEDICAL DEVICE WITH TRIGGERED BLANKING PERIOD, as well as other patent publications. Illustrative architectures may also resemble those found in the Micra™ (Medtronic) or Nanostim™ (St. Jude Medical) leadless pacemakers.

The device is shown with a first end electrode at 114 and a second end electrode at 116. A number of tines 118 may extend from the device in several directions. The tines 118 maybe used to secure the device in place within a heart chamber. Another attachment structure is shown at 120 and may take the form of a helical screw, if desired. In some examples, tines 118 are used as the only attachment features. Tissue attachment and retrieval features may be included in the LCP including those features shown in US PG Patent Publications 20150051610, titled LEADLESS CARDIAC PACEMAKER AND RETRIEVAL DEVICE, and 20150025612, titled SYSTEM AND METHODS FOR CHRONIC FIXATION OF MEDICAL DEVICES, the disclosures of which are incorporated herein by reference. Fixation and retrieval structures may instead resemble that of the Micra™ (Medtronic) or Nanostim™ (St. Jude Medical) leadless pacemakers.

Figure 4:
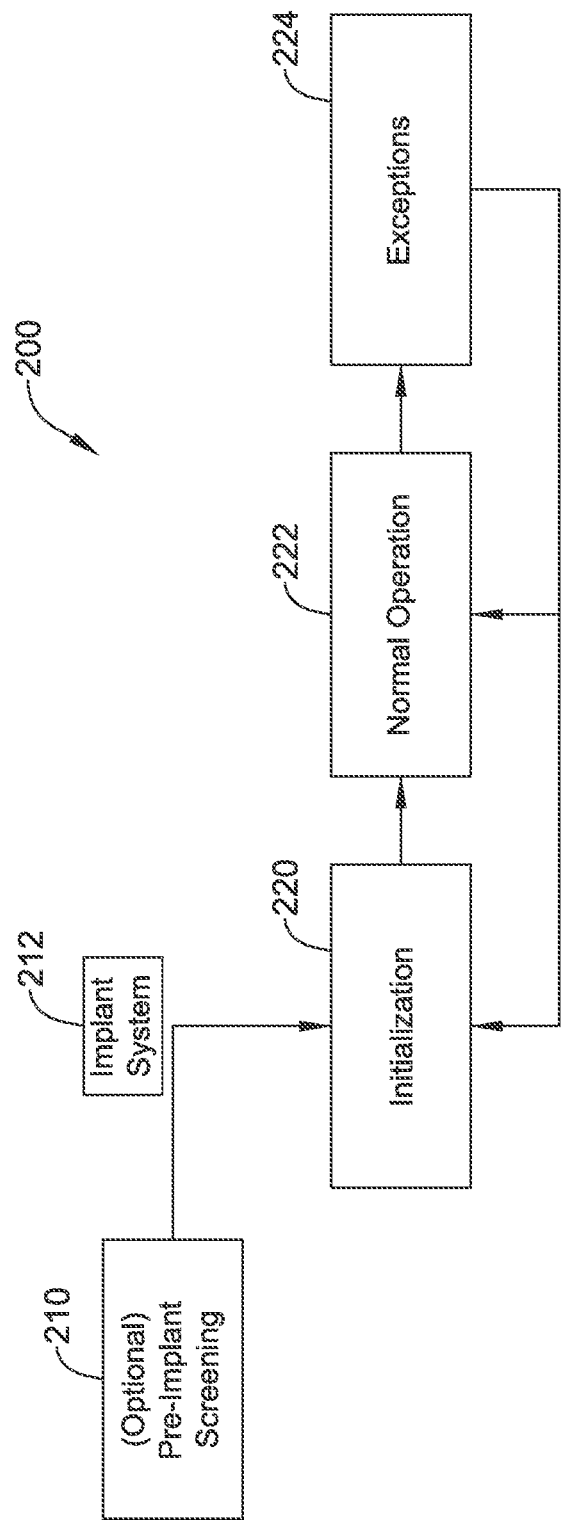
FIG. 4 shows an overall method of use of a system.

FIG. 4 shows an overall method of use of a system. The method 200 in this case goes back, optionally, to pre-implant screening, as indicated at 210. For example, the implantation of an SICD may occur following pre-implant screening for cardiac signal amplitude and/or signal to noise ratio, and/or to determine whether the patient's routine cardiac rhythm will be well managed using an SICD. Some example screening tools, metrics and methods discussed in U.S. Pat. No. 8,079,959, titled PATIENT SCREENING TOOLS FOR IMPLANTABLE CARDIAC STIMULUS SYSTEMS, and/or US Patent Application PG Pub. No. 20160296131, titled AUTOMATED SCREENING METHODS AND APPARATUSES FOR IMPLANTABLE MEDICAL DEVICES, the disclosures of which are incorporated herein by reference.

Pre-implant screening may also determine whether the patient is well suited to have a combined LCP/SICD or LCP/SCM system for CRT by assessing the presence or absence of a P-wave. P-wave related screening may be optional with the present invention, as various examples rely on SICD or SCM analysis of the QRS complex (or other cardiac signal) to confirm fusion, rather than the appearance or timing of the P-wave, to enhance or control CRT to attain desirable fusion.

The system(s) are then implanted at 212. Implantation may include the placement of an LCP on or in the heart, as well as placement of an SCM or SICD elsewhere in the patient such as between the ribs and the skin. The system may undergo intraoperative testing as is known in the art for each of LCP, SCM and SICD devices, to ensure adequate sensing configurations and/or therapy capability.

Next, the system undergoes initialization, at 220. Initialization may include, for example, the setting of various sensing and other parameters. Examples of initialization may include selecting of a sensing vector or combination of sensing vectors, such as in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843 SENSING VECTOR SELECTION IN A CARDIAC STIMULUS DEVICE WITH POSTURAL ASSESSMENT, the disclosures of which are incorporated herein by reference. Related concepts surrounding the use of multiple vector sensing are also disclosed in US PG Patent Pub. Nos. 2017/0112399, 2017/0113040, 2017/0113050, and 2017/0113053, the disclosures of which are incorporated herein by reference. Methods as discussed in US PG Patent Pub. No. 2017/0156617, titled AUTOMATIC DETERMINATION AND SELECTION OF FILTERING IN A CARDIAC RHYTHM MANAGEMENT DEVICE, the disclosure of which is incorporated herein by reference, may be used as well for setting filtering characteristics.

Initialization for an LCP may also include the setting of parameters for therapy including, for example, selecting pace shape, pulsewidth and/or amplitude. If plural LCPs are included in a system, the relative timing between pace deliveries amongst the plural LCPs, and other suitable features, may be set as well. Initialization may also include identifying a P-R interval for the patient, which can be done and used as discussed below relative to FIG. 6.

Once initialization 220 is completed, normal operation can occur as indicated at 222. Such operation may include CRT delivery in which a first device delivers pacing pulses for CRT purposes with the assistance of a second device such as an SICD or SCM.

FIGS. 5-8 show a number of illustrative approaches to pacing and pace timing for CRT in a multi-device implantable system. Such approaches are referred to herein as modes of pacing for CRT. Different modes use different inputs or criteria for determining whether and/or when a pace therapy (a single pace impulse of a monophasic, biphasic, or other shape voltage or current controlled therapy output associated with a single cardiac cycle) is to be delivered. Any of the modes of pacing for CRT shown in FIGS. 5-8 may be used as a "normal operation" at 222 in FIG. 4, though different modes of pacing for CRT may have different initialization needs. Multiple pace therapies, as used herein, means multiple individual paces, as opposed to pacing via different configurations or for different purposes.

Some of the following examples call for each of an extracardiac device, such as an SICD or SCM to provide information or commands to an implanted LCP such as an LCP placed in the left ventricle of a patient. Some examples instead call for the LCP to perform its own assessments to perform pacing as needed. The aim in several examples is to provide effective CRT. In keeping with the spirit of the present invention, other modes than those shown may be used.

Figure 5:
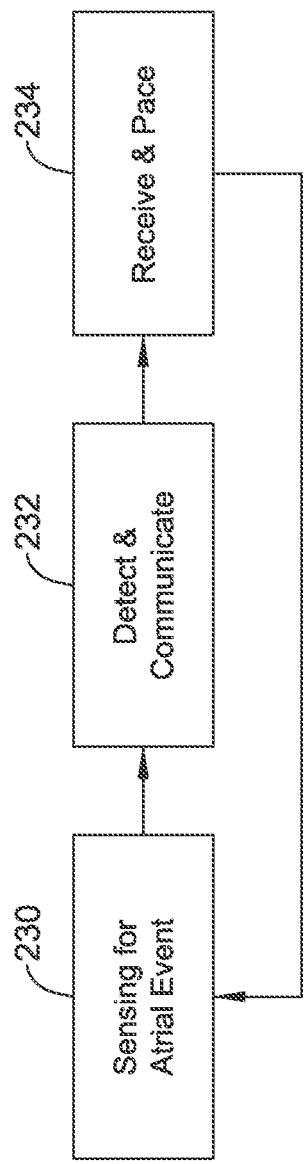
FIGS. 5-8 show a number of illustrative approaches to pacing and pace timing for a multi-device implantable system.

FIG. 5 shows a mode in which an extracardiac device, such as an SICD or SCM, or a second implantable LCP, performs sensing for an atrial event 230, detects the atrial event and communicates to the LCP at 232. The LCP receive the communication and delivers pacing at 234. The LCP may be located in the left ventricle. The communication may take the form of a command to pace, or may instead simply provide information such as a notification that an atrial event has been sensed.

The atrial event may be an electrical signal detection, such as a P-wave, or likely P-wave, has been detected. See, for example, U.S. patent application Ser. No. 15/633,517, titled CARDIAC THERAPY SYSTEM USING SUBCUTANEOUSLY SENSED P-WAVES FOR RESYNCHRONIZATION PACING MANAGEMENT, the disclosure of which is incorporated herein by reference, for examples using a second device to detect an atrial electrical signal for use in CRT pacing. The atrial event may be a mechanical event instead, indicating atrial contraction. See, for example, U.S. patent application Ser. No. 15/642,121, titled METHOD AND SYSTEM FOR DETERMINING AN ATRIAL CONTRACTION TIMING FIDUCIAL IN A LEADLESS CARDIAC PACEMAKER SYSTEM, the disclosure of which is incorporated herein by reference, for examples of the LCP or a second device detecting an atrial mechanical signal for use in CRT pacing. For example, the S4 heart sound, which indicates atrial contraction may be detected and relied upon. In another example the A-wave, a pressure wave indicating atrial contraction, may be detected and relied upon.

The electrical P-wave or other atrial event sensing may be difficult in some environment such as a noisy environment, or may be difficult in certain patients due to abnormal conduction, placement of sensing electrodes, etc. P-wave or other atrial event sensing may also be difficult if a patient has an atrial arrhythmia that prevents such sensing, for example, if a patient starts to experience atrial fibrillation. Patient movement and/or the patient's environment may affect the ability to sense a mechanical signal as well. Thus accommodations to adjust for any changes, as well as the capacity to identify a need for adjustments, may be useful.

Figure 6:
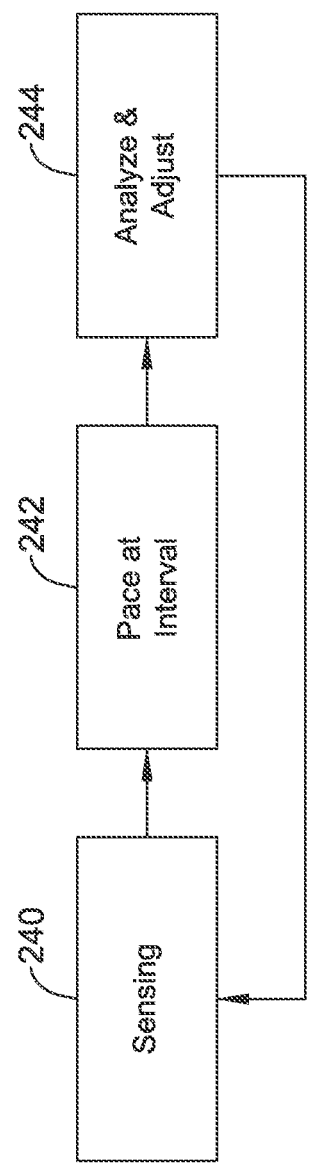

FIG. 6 shows another illustrative example in which sensing is performed by an extracardiac device such as an SICD or SCM or by a second LCP, as indicated at 240, across an interval of time during which a pace therapy is then delivered at 242 by an LCP which may be a left ventricular LCP. The sensed signal from block 240 is then analyzed and adjustments may then be made to the interval used for pace timing at block 242. For example, an interval from the pace therapy delivery to the R-wave, to the QRS complex, or from the P-wave to the pace therapy, may be calculated and/or assessed retrospectively to then make adjustments to tailor the desired timing. See U.S. patent application Ser. No. 15/684,366, titled INTEGRATED MULTI-DEVICE CARDIAC RESYNCHRONIZATION THERAPY USING P-WAVE TO PACE TIMING, the disclosure of which is incorporated herein by reference, for retrospective analysis of such features. Rather than an electrical signal analysis, the sensing at 240 may use mechanical sensors (an accelerometer, or pressure sensor for example) to find the timing of an atrial mechanical event.

Figure 7:
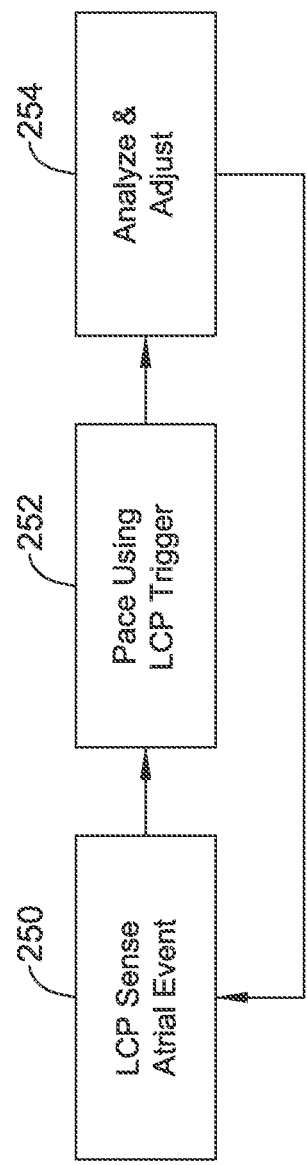

FIG. 7 shows another illustrative example of a pace timing mode. Here, an LCP senses an atrial event at 250 and delivers pacing using a trigger sensed by the LCP itself, as indicated at 252. A second device, such as a second LCP or an extracardiac device such as an SICD or SCM then analyzes the signals and calculates adjustments as indicated at 254. For example, the second device may reference an electrical signal (cardiac electrical signal), a mechanical signal (motion or pressure/sound sensor), or a physiological measure (pulse oxygenation) to perform analysis, and the analysis may include measuring outcomes (fusion morphology, or desired amount of motion or pressure change, volume change, or sounds) or parameters (the P-wave to Pace or Pace to R-wave duration, for example). In some alternative examples, the device that paces at 252 may also perform the analysis and adjustments at 254.

Figure 8:
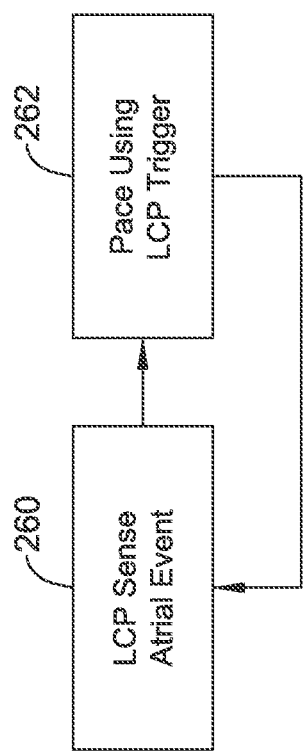

FIG. 8 shows an example in which the LCP senses an atrial event, either using mechanical or electrical signals, as indicated at 260. In response, the same LCP delivers a pace therapy at a time selected relative to the atrial event, as indicated at 262. For example, the LCP may rely on a heart sound (such as showing valve opening or closing in response to an atrial motion), a pressure waveform (such as a change in pressure based on atrial contraction), an electrical cardiac signal (such as sensing a P-wave), a motion signal (such as sensing movement caused by atrial contraction), an impedance measurement (such as sensing a change in impedance cause by a change in cardiac volume), or an optical signal (such as sensing blood motion due to atrial contraction).

Figure 9:
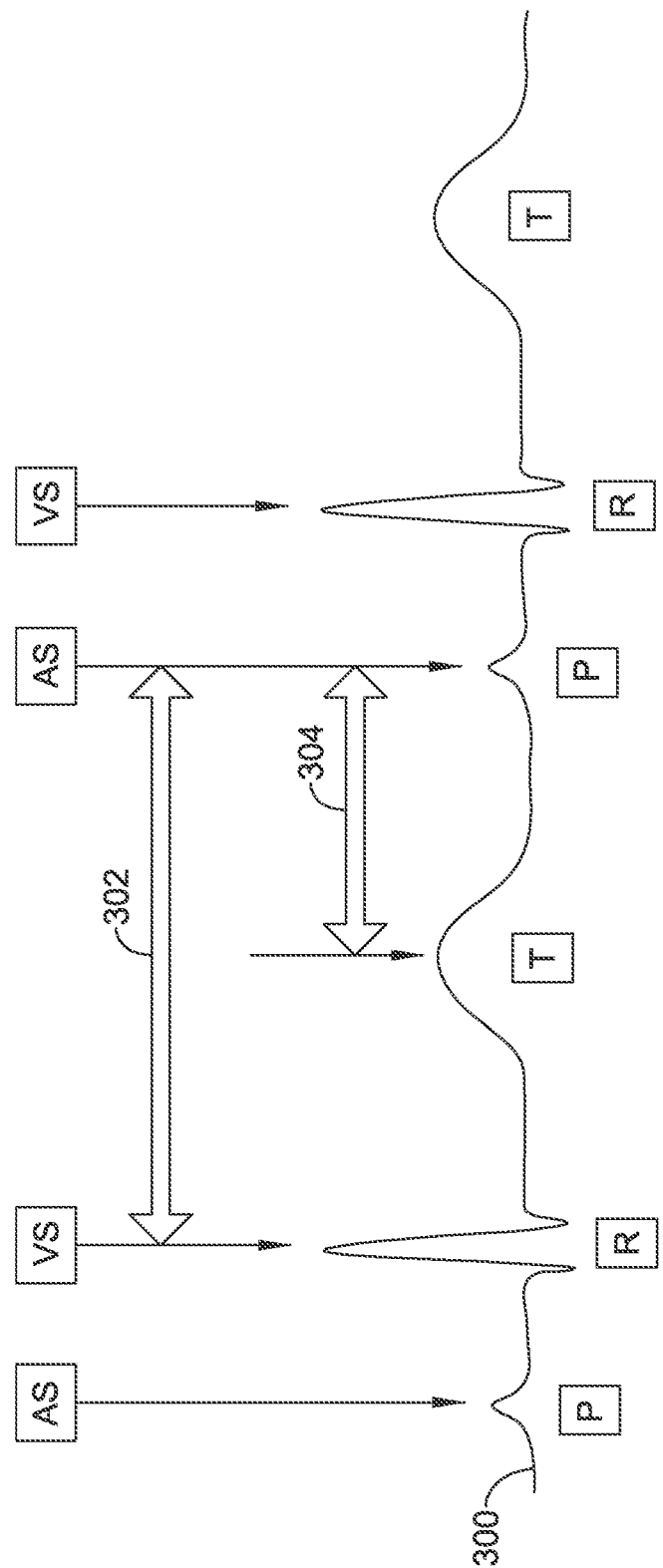
FIG. 9 highlights certain features of a cardiac electrical signal.

FIG. 9 highlights certain features of a cardiac electrical signal. A far field representation (that is, a signal captured using only electrodes that are neither in nor on the heart) is shown with trace 300. The trace 300 is marked using standard convention with the P-wave, R-wave (which, when combined with preceding Q-wave and following S-wave may be referred to as the QRS complex), and later T-wave. The P-wave represents atrial depolarization associated with atrial contraction to load the ventricles, the R-wave or QRS complex (the unmarked downward deflections) represents ventricular depolarization of the ventricles contracting to pump blood to the body and lungs, and the T-wave is associated with the electrical activity that repolarizes the ventricular muscle in preparation for a next beat. With heart failure and/or dysynchrony, the timing of these individual events may be anomalous or abnormal, and the shape of depolarization waves can be different from that shown, for example, by having a much wider QRS complex or R-wave as the left and right ventricles depolarize in a poorly coordinated manner.

With traditional CRT systems having transvenous leads, the intracardiac electrodes are placed to detect the atrial depolarization while also delivering resynchronizing pacing therapy to one or both ventricles. As a result, the circuitry of a single device would directly receive information for the P-wave, allowing delivery at a timed interval of a pacing pulse to the ventricle. This can be done to achieve fusion—synchrony of the electrical signals arriving in the ventricles, to resynchronize contractions and improve pumping efficiency. However, with a system as in FIG. 1, the LCP may be unable to identify the P-wave generated in the atria from an implanted location in the ventricle. Therefore the LCP, in several embodiments of the present invention, relies on a second medical device such as a subcutaneous cardiac monitor or SICD to determine whether and when the P-wave occurs.

The SICD (or subcutaneous cardiac monitor or other extracardiac device (ED)) may be optimized for detection of R-waves and/or QRS complexes, in order to ensure that deadly arrhythmias (ventricular fibrillation and/or polymorphic ventricular tachycardia) can be appropriately and quickly identified. P-waves may be detected using separate parameters and/or analysis from R-wave detection for such a device. In some examples, a time window for P-wave detection is defined during which the ED may specifically look for the P-wave. Such windows may be defined by analysis of the cardiac signals obtained from a patient using, for example, a ventricular event such as the R-wave/QRS complex or the T-wave as the starting point for timing delays 302, 304 shown in FIG. 9. Durations 302, 304 may be dynamic to adjust to the overall beat rate of the patient using data gathered from a patient or using a formula or accepted relationship.

The ED may use a dedicated sensing configuration to separately detect ventricular events and a second, separately defined dedicated sensing configuration to separately detect atrial events. For example, the Emblem™ S-ICD system performs vector selection to identify a sensing vector having optimal R-wave amplitude and signal to noise ratio as a default vector for sensing the patient's cardiac rhythm, as disclosed for example in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843 SENSING VECTOR SELECTION IN A CARDIAC STIMULUS DEVICE WITH POSTURAL ASSESSMENT, the disclosures of which are incorporated herein by reference. Related concepts are also disclosed in US PG Patent Pub. Nos. 2017/0112399, 2017/0113040, 2017/0113050, and 2017/0113053, the disclosures of which are incorporated herein by reference. In an example, a second vector selection and/or sensing configuration process may be used to determine how the P-wave will be detected by a given device.

In further examples, filtering, gain, or other characteristics may be selected specific to P-wave detection. For example, if a ventricular event sensing channel uses a first passband, a P-wave sensing channel passband may be set to a different passband. For example, the R-wave or ventricular event passband may be set in the range of 3-40 Hz, or 9-40 Hz, or other setting. The P-wave passband may be set to a different range, for example, 0.5 to 20 Hz. Such band setting and selection may be partly contingent on reviewing the captured signal of either or both of ventricular and/or atrial events. Methods as discussed in US PG Patent Pub. No. 2017/0156617, titled AUTOMATIC DETERMINATION AND SELECTION OF FILTERING IN A CARDIAC RHYTHM MANAGEMENT DEVICE, the disclosure of which is incorporated herein by reference, may be used to select a sensing channel passband(s). In another example, a passband may be varied until signal amplitude for the desired atrial or ventricular feature begins to drop, at which an edge or corner of the passband may be set, to achieve a targeted, narrow passband. Thus a P-wave sensing or atrial sensing configuration may use a different frequency band than a corresponding R-wave sensing or ventricular event filter. Alternatively, a single passband may be set for use in each of atrial and ventricular sensing, or different pre-set ranges may be used for each of atrial and ventricular sensing Setting the sensing configuration for detecting P-waves may thus include either or both of setting a detection window and/or selecting filter or vector configurations. In addition, the actual manner of detecting the P-wave is defined in some illustrative examples as part of the sensing configuration. For example, the P-wave may be detected by comparing a detected signal to a fixed or time-varying amplitude threshold. In another example, the P-wave may be detected by comparing segments of captured signal to a template until a match is found or at timeout occurs. When a match is found a P-wave detection can be declared; if a timeout occurs, it may be concluded that the P-wave was not present or simply not seen. In some examples, more than one method of identifying P-waves may be available for use, and a most effective approach for a given patient may be selected. For example, if amplitude threshold and template match approaches to P-wave detection are available, a patient having highly variable amplitude signals may have his or her device configured to use the template match approach rather than an amplitude based approach.

In some examples, a possible P-wave is confirmed as such prior to generating an output communication. For example, a template of the P-wave may be defined and used to confirm whether a detected signal that crosses an amplitude threshold is in fact a P-wave by comparing the detected signal to the template. Such templates may be static and stored in memory, may be matched from one beat to the next by comparing a first in time P-wave to a next in time possible P-wave, or may be a hybrid of a stored template and fully dynamic template as by, for example, averaging in newly detected P-waves to a template.

In some examples, patients may be pre-screened for P-wave availability with the second medical device that is to be used for synchronizing LCP pacing. For example, it may well be that due to anatomical variations or other factors, some patients will have a well-defined P-wave providing a ready fiducial for the SICD or subcutaneous cardiac monitor to rely upon to prompt CRT therapy by an LCP. In other patients, the P-wave may be difficult to detect consistently. Thus a pre-screening process may be performed, either as an in-clinic test, or by having a patient use a Holter monitor or by implanting a subcutaneous cardiac monitor to ensure that the P-wave is readily identified consistently.

Figure 10:
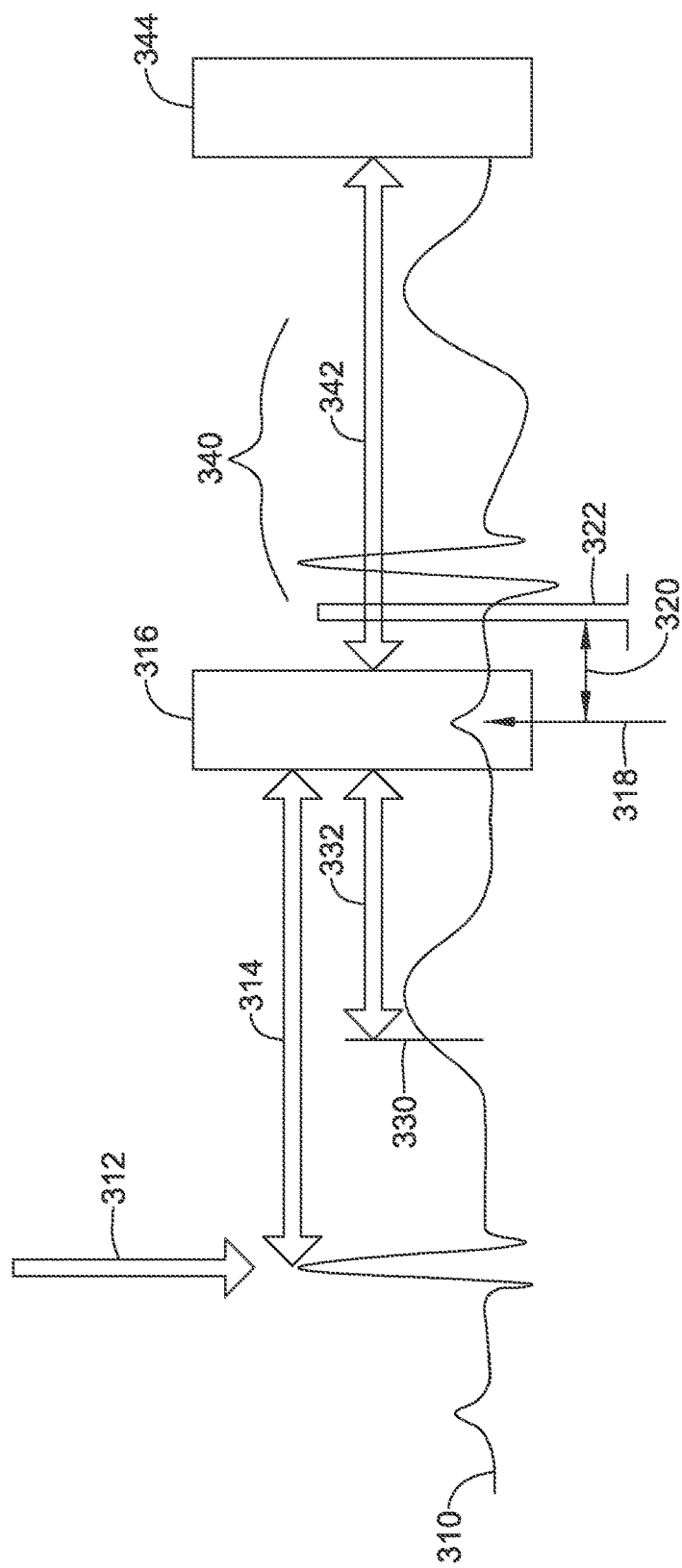
FIG. 10 illustrates setting of a P-wave detection window.

FIG. 10 illustrates setting of a P-wave detection window showing at least one of the above concepts in action. Here, a trace is shown at 310 and includes the features indicated in FIG. 9 for two cardiac cycles. An R wave and QRS complex are identified at 312. The device uses an interval 314 to then trigger a P-wave detection window 316 for identifying the P-wave 318 of the cardiac signal. As illustrated here, the P-wave detection window 316 is useful insofar as the P-wave is smaller than other cardiac features, but also occurs after a relatively quiet time period following the T-wave. The P-wave detection window 316 may alternatively be triggered from the T-wave 330, using an interval 332, if desired. The intervals based on T-wave or R-wave detection may start from an inflection point, a peak, a threshold crossing, or any other desired, preferably repeatable, fiducial point of the underlying T-wave or R-wave.

Detection of the P-wave 318 is used to trigger another interval 320, after which a ventricular pace therapy is delivered at 322. Interval 320 may be variable and is used to trigger the pace therapy to allow fusion—whereby the natural conduction signals of the heart reach one ventricle at about the same time as the pace therapy is delivered to the other ventricle, for example, to allow coordinated ventricular contraction.

In some examples, an ED detects the P-wave 318, and the interval 320 is consumed, at least in part, by the time required to communicate to an LCP and trigger the LCP to deliver the pace 322, such as discussed in U.S. patent application Ser. No. 15/633,517, titled CARDIAC THERAPY SYSTEM USING SUBCUTANEOUSLY SENSED P-WAVES FOR RESYNCHRONIZATION PACING MANAGEMENT, the disclosure of which is incorporated herein by reference.

In some examples, the LCP delivers the pace therapy 322 using a calculated interval relative to, for example, a prior delivered pace therapy or a prior detected fiducial such as the R-wave 312, and the ED and/or LCP detect cardiac signal features such as the P-wave in order to manipulate the calculated interval to achieve a desired P-wave to Pace interval 320. See U.S. patent application Ser. No. 15/684,366, titled INTEGRATED MULTI-DEVICE CARDIAC RESYNCHRONIZATION THERAPY USING P-WAVE TO PACE TIMING, the disclosure of which is incorporated herein by reference.

Looking closely at the drawing, the skilled artisan will appreciate that the unpaced QRS complex at 312 has a different morphology than the paced complex following pace therapy 322, with the Q-wave deflection more pronounced, and the S-T interval having a different shape. Such changes can be monitored to determine whether pace therapy is having an intended effect, as explained in U.S. patent application Ser. No. 15/684,264, titled CARDIAC RESYNCHRONIZATION USING FUSION PROMOTION FOR TIMING MANAGEMENT, the disclosure of which is incorporated herein by reference. After the first pace therapy is delivered 322, the method can shift to using a different interval, if desired, to trigger the start of the P-wave sensing window at 344, using, for example, an interval from a prior P-wave window as indicated at 342, or using an interval from the pace therapy 322, or, alternatively, using the interval from the R-wave peak or T-wave peak as before.

Figure 11:
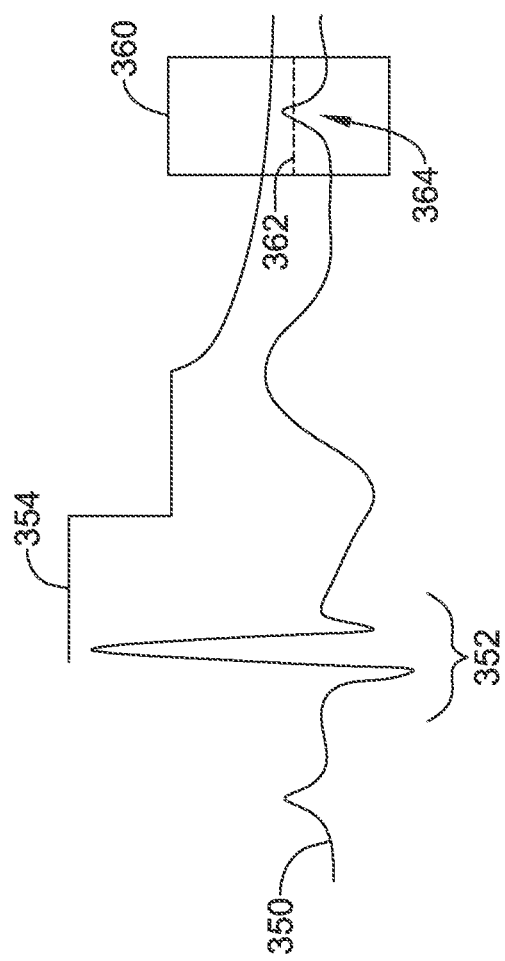
FIGS. 11-12 show a use of a P-wave detection window.
Figure 12:
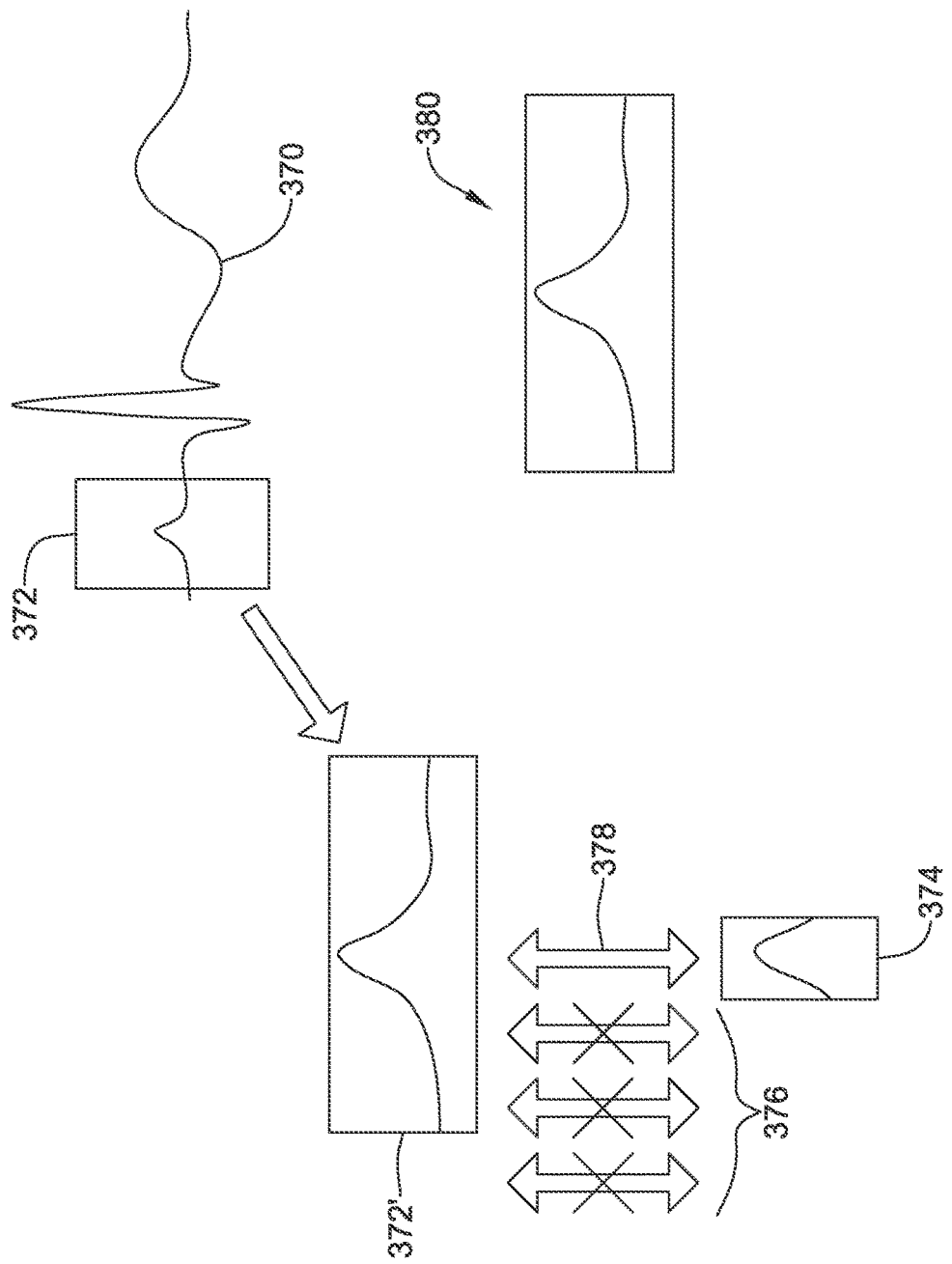

FIGS. 11-12 show a use of a P-wave detection window. FIG. 11 shows a first example in which the trace 350 includes a paced complex 352 that is used to trigger an R-wave detection threshold 354 similar to that shown in U.S. Pat. No. 8,565,878, titled ACCURATE CARDIAC EVENT DETECTION IN AN IMPLANTABLE CARDIAC STIMULUS DEVICE, the disclosure of which is incorporated herein by reference. It can be seen that this detection threshold 354 is configured to avoid detecting the T-wave (not marked) as well as the P-wave 364.

A P-wave detection window is provided at 360. A separate P-wave detection threshold 362 is defined within the P-wave detection window 360. The P-wave detection threshold 362 may be a flat threshold or it may vary with time, if desired. For example, a P-wave detection threshold 362 may be a percentage of the R-wave detection threshold 354.

FIG. 12 shows another example of P-wave detection. Here, a cardiac signal is shown at 370 with a P-wave detection window at 372. The signal in window 372 is expanded as shown at 372'. A P-wave template is shown at 374. To detect the P-wave, a series of comparisons are made as incoming signal is received. Once enough signal is received to perform a morphology comparison, such as by difference of area, correlation waveform analysis, wavelet transform, or principal components analysis, for example, a morphology comparison is made. The morphology comparison is repeated as indicated at 376 as more signal comes in, with data entering a comparison window on a first-in, first-out basis, until a match is found at 378. Match 248 is then the P-wave detection. In another example, indicated at 380, the correlation of the series of comparisons 376 can be mapped across the duration of the P-wave detection window 372, and the peak correlation may be identified to correspond to the time of the P-wave occurring.

In still further examples, a P-wave detection window 372 may be searched to identify a specific feature associated with a possible P-wave. For example, a P-wave may be identified by observing whether a slope in excess of a threshold and with a minimum pathlength occurs during the P-detection window.

Figure 13:
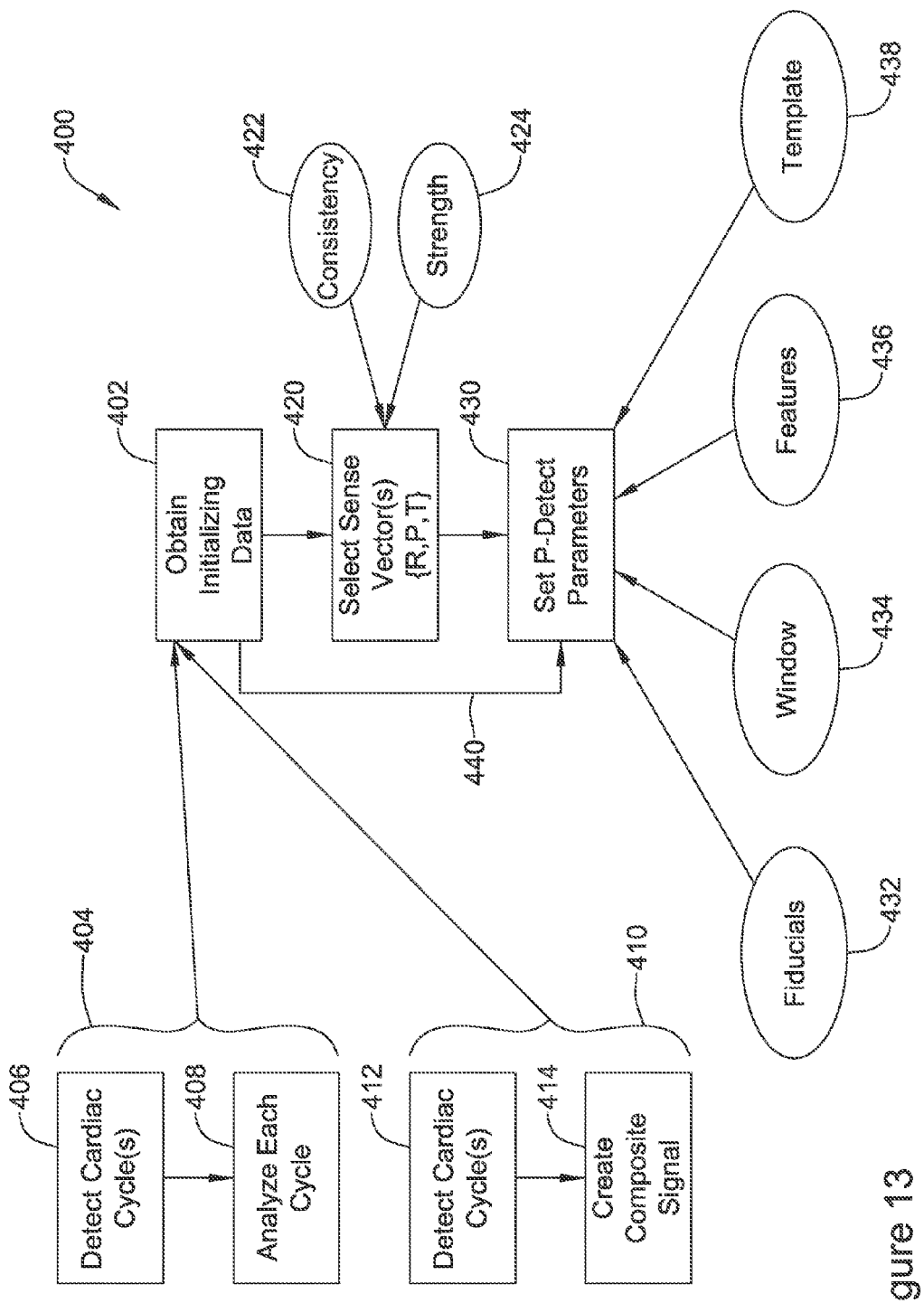
FIG. 13 illustrates a method of configuring sensing in one or more devices.

FIG. 13 illustrates a method of configuring sensing in one or more devices. In the example method 400, initializing data is obtained as indicated at 402, and one or more sensing vectors are selected, as indicated at 420. Next, the detection parameters such as parameters for detecting P-waves or atrial events (P-Detect Parameters) are set, as indicated at 430. Generally speaking, steps 402, 420 and 430 may be performed by an SICD, SCM, or other ED, or by an LCP, as desired and based on which device, in a particular implementation, is to detect which of the R, P, or T waves and/or QRS complex.

The step of obtaining initializing data at 402 may include various subprocesses as indicated on the left side of FIG. 13. For example, as indicated at 404, a plurality of individual cardiac cycles may be detected at 406 in one or several sensing vectors or with one or several different sensing configurations (affecting for example, filtering and/or amplification parameters, possibly in combination with vector selection parameters). The individual detections of cardiac cycles may be analyzed 408 by, for example, binning different detected data elements from each cycle as discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH. As an alternative shown at 410, a set of cardiac cycles are detected as indicated at 412 and a composite signal is generated as shown at 414. The use of a composite signal to establish sensing vector quality metrics is discussed, for example, in US PG Patent Application Pub. No. 20170113053, titled SIGNAL QUALITY MONITORING FOR MULTIPLE SENSE VECTORS IN CARDIAC DEVICES, the disclosure of which is incorporated herein by reference.

Next, in block 420, sense vector configurations for ventricular (targeting, for example, R waves, the QRS complex, and/or T-waves) and/or atrial event detection (targeting, for example, the P-wave) are selected. The vector configuration may include selecting combinations of electrodes to use, combinations of two or more vectors to use together, and/or the setting of filtering, blanking, refractory, amplification or other parameters. Various approaches to vector selection may be used including those referenced above from other patents or patent applications, as well as those discussed herein. For example, consistency of a vector configuration may be used, as indicated at 422, to select a given vector. Consistency 422 may mean, for example, that a selected cardiac event (P, R or T waves, or the QRS complex) is consistent in shape, amplitude and/or timing, in a given vector configuration. Alternatively or in combination with consistency, strength 424 of the signal, absolute and/or relative to noise may be considered as well.

In some examples, once vector configuration is set, the parameters for identifying P-waves are set as indicated at 430. In an alternative, as indicated by the line at 440, the sensing configuration step may be bypassed, and P-Detect parameters set at 430. For example, block 420 may be performed in some embodiments only when connected to a clinician programmer to ensure that appropriate signals are obtained and/or that sensing configuration is not modified contrary to known patient history, while blocks 402 and 430 may be performed by a device independent of programmer intervention. In some examples, on the other hand, block 430 may be omitted, with the sensing vector setup performed and any suitable method of P-wave detection used by the device without necessarily performing a separate optimization at 430.

Block 430 calls for setting one or more parameters to optimize P-wave detection. In some examples, this may include selecting one or more of the fiducials from which P-wave detection is triggered, at 432, setting a window for detecting the P-wave 434, selecting the features to look for when attempting to detect a P-wave 436, or selecting a template for P-wave confirmation at 438. Any of blocks 432, 434, 436, 438 may be used in various combinations or, in some examples, standing alone.

For example, the fiducial selection at 432 may be used to select a feature (whether atrial or ventricular, such as an R-wave, a T-wave, a preceding P-wave, or other physiological, such as a heart sound, a blood pressure signal, or other timing point of reference such as delivery of a pacing pulse), that starts a blanking period during which P-waves cannot be detected, for example, to pass over the T-wave, and upon expiration of the blanking period, P-wave detection is enabled. Alternatively, the fiducial 432 may be used to trigger the initiation of an analysis window for the P-wave. The window 434 may be used as shown above in FIGS. 10-12 by, for example, determining relative to a selected fiducial point when the P-wave typically appears and then setting a window of a duration equal or longer than the P-wave for allowing P-wave detection. The window may be, for example, about 50 to 400 milliseconds. In another example, the window may be about 100 to about 200 milliseconds. Other durations may be used.

Which features to use for identifying the P-wave is another element, as indicated at 436. For example, a P-wave may be identified by having an amplitude of a certain range, such as greater than a threshold. A threshold may be adaptive to current patient conditions by, for example, setting it to some percentage (50% to 90%, or more or less) of a preceding P-wave or an average of several preceding P-waves, or stored information relating to typical P-waves generally or specific to a given patient. Other features may include a maximum or minimum slope amplitude or length. In an example, the P-wave may be identified by the detected signal moving in a certain direction within predefined slope parameters for at least a predetermined amplitude or period of time. Thus, for example, the signal may have an upward slope that is characteristic of the P-wave, not so steep as for the R-wave, but steeper than the T-wave, of at least a select duration to avoid noise detection. Slope analysis may take place by using the first or second derivative of the obtained signal. Other features may be used instead at block 436.

The template 438 may also be used independent of other items to detect a P-wave. For example, the template may be compared to received data on a continuous or semi-continuous basis, and when a match is found, a P-wave may be declared (see FIG. 12, above). Alternatively, a series of comparison results may be compared to select a peak correlation. The template may be an averaged composite of prior signals, or may be simply a prior P-wave, or may be constructed in any other suitable manner. The incoming signal itself may be a signal averaged composite of several cardiac cycles having, for example, P, Q, R and S signals (and T-waves if the composite is so configured).

In an example, during a window defined using 434 based on a fiducial 432, a template may be compared to an incoming data stream to identify a match. In other examples, the template 438 may be used to confirm a detected likely P-wave, such as a signal that crosses a defined amplitude threshold during a P-wave detection window. If the template 438 matches the likely P-wave, then P-wave detection is confirmed or, alternatively, if there is no match to the template 438, then the threshold crossing/detection may be discarded as not being a P-wave.

Figure 14:
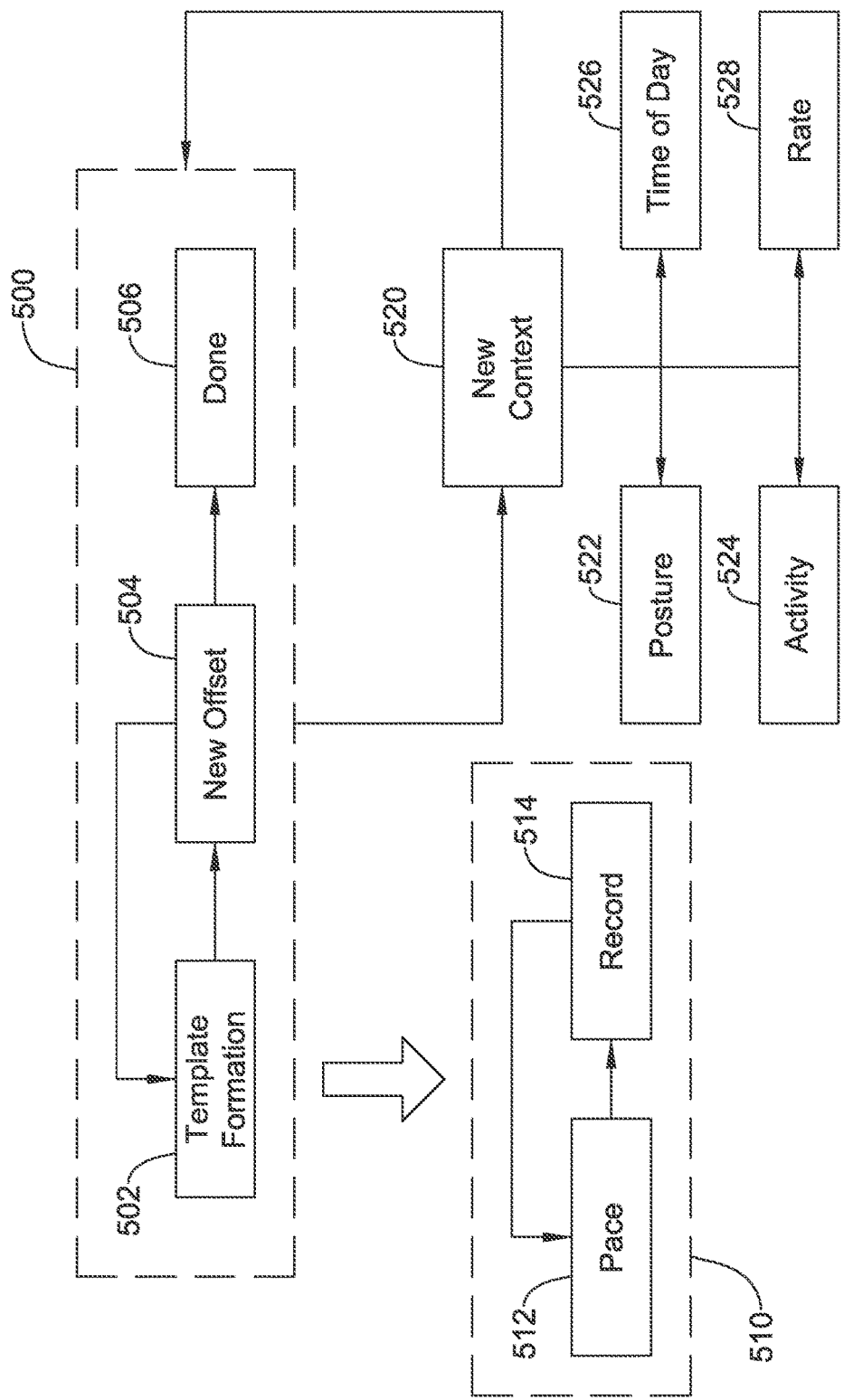
FIG. 14 illustrates a method for setting templates in an illustrative example.

FIG. 14 illustrates a method for setting templates in an illustrative example. The example includes an iterative process for generating related templates indicated at 500, as well as a pace and record process 510. In the illustration, a template formation block 502 is called and activates the pace/record block 510. To form the template, one or several pace outputs 512 are generated, and an associated signal is recorded 514. The associated signal 514 may take a variety of forms such as those indicated below in FIG. 18, including cardiac electrical, sound, pressure, motion, impedance and/or optical signals.

In one example, a single pace output is generated at block 512 and the resulting signal is recorded at 514. In other examples, a number of pacing outputs are generated using what are considered "optimal" parameters to achieve desired outcomes, and several resulting signals are recorded at block 514 and averaged together to yield a template. If desired, statistics may be calculated associated with the template to provide indications of a range of variation that is expected. In some examples, the template may be validated by comparing several outputs to ensure similarity of the recorded signal over each of several pace outputs; if the recorded signal at 514 varies without variation of the pacing parameters, the template is likely of little use, as it may be unable to distinguish variation due to changing pacing parameters from variation occurring within desired pacing parameters, and such a template may be discarded, generating an error message. If a template cannot be validated for a given signal type, the system may elect to use a different signal type, such as by switching from use of a motion signal to a heart sound.

Once a given template is formed at block 502, the process 500 repeats at a new offset 504. In some examples, a fixed offset shifting the pace therapy earlier or later in time may be used, such as by shifting 20 milliseconds in each direction around a preferred, non-offset pace timing. In some examples, a plurality of offsets may be tried, such as by adjusting in modest increments (such as by offsetting 5 milliseconds a number of times) until a template is formed that does not match the first-formed template. In some examples a one-sided approach is used by delivering the pace therapy earlier in time, or later in time, than the preferred configuration, without forming a second template. In other examples, three total templates are formed—a preferred configuration template, an early template representing an outcome that would occur if pace therapy is too early to yield a desired outcome, and a late template representing an outcome that would occur if pace therapy is delivered too late to yield a desired outcome. In still other examples, more than three templates may be formed.

When process 500 is done 506, the results may optionally be stored in association with a specific context. The process 500 can then be repeated for a plurality of different contexts as indicated at 520. By context, what is meant is that the device is operating in a specific physical or other circumstance that may affect the usefulness of a particular template or set of templates. For example, a given sensor output may vary in response to one or more of posture 522, activity level 524, time of day 526, and/or the underlying cardiac rate 528. As specific examples, cardiac impedance metrics may vary with patient posture 522, and motion signals can vary with patient activity level, while pressure metrics may be affected by time of day 526, and/or cardiac electrical metrics, including those reliant on intervals between peaks or other events, may be affected by the underlying cardiac rate 528. Changes in patient activity may be determined by monitoring outputs of a motion sensor using known methods; changes in cardiac activity may also be determined using a temperature sensor in the patient's bloodstream, if desired; such changes may be determined or confirmed as well using the patient's intrinsic cardiac rate which may be determined by stopping CRT delivery for a number of cardiac cycles from time to time. An accelerometer output may be monitored using known methods to determine patient posture and/or changes in patient posture. The time of day may be determined from a system clock. The patient's cardiac rate may be determined using R-wave detection or other rate measurement methods such as disclosed in U.S. Pat. No. 8,565,878 and/or US PG Patent Publication Nos. 20160045136, 20160045132, and 20160045131, the disclosures of which are incorporated herein by reference as showing one or more of rate calculation and/or cardiac cycle detection.

Optionally, the process at 500 may be repeated for a plurality of different contexts 520 as those are detected or identified. If desired, a set of contexts may be actively induced such as by having the patient change posture while template steps 500 are performed, or having the patient exercise to achieve activity 524 or rate 528 changes.

Rather than a template being formed in block 502, target measurements or value boundaries may be gathered in another example. For example, target peak amplitudes, slopes or magnitudes, widths, maxima, minima, or intervals between detected events of similar or dissimilar types may be captured in the record step 514. Such targets may developed in similar fashion to that shown, with different offsets tested to establish boundaries between desirable outcomes, undesirable outcomes, and outcomes that are not within a captured range. FIG. 27 shows an example. When value boundaries are gathered, different value boundaries may be determined for different contexts as indicated at block 520.

Figure 15:
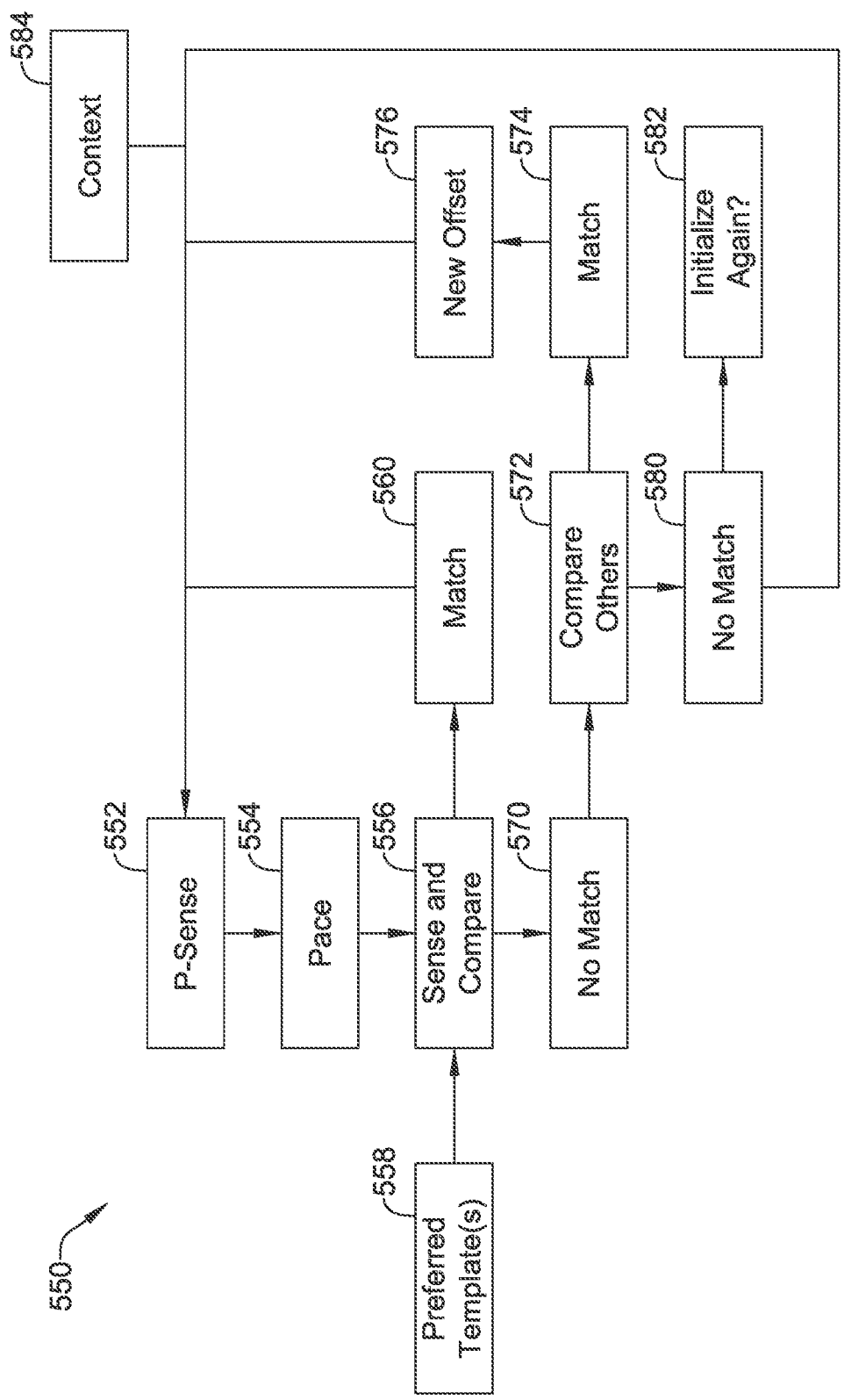
FIGS. 15-16 show methods of monitoring and enhancing P-wave detection.
Figure 16:
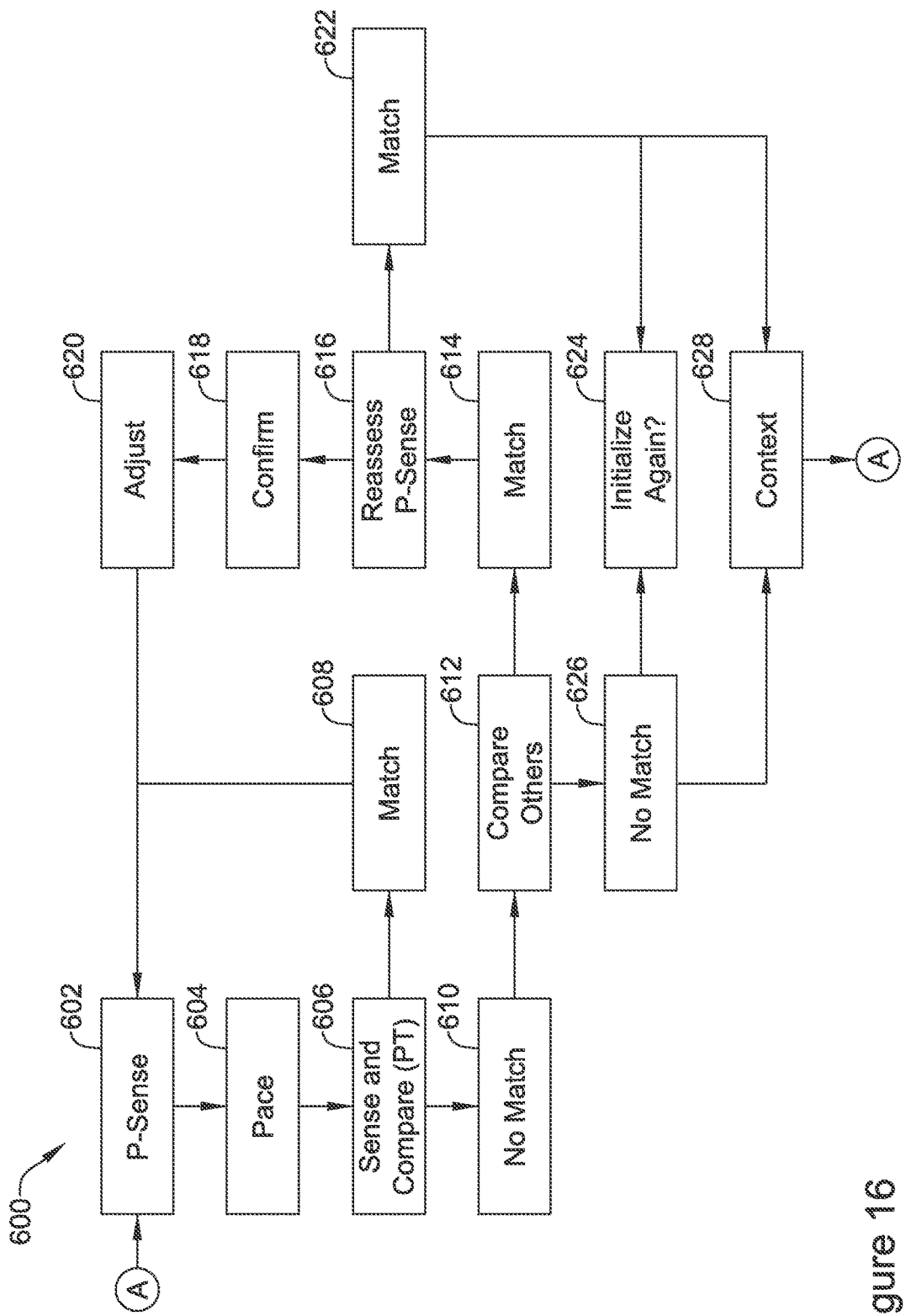

FIGS. 15-16 show methods of monitoring pacing outcomes and enhancing P-wave detection. The illustrative method 550 begins with sensing a P-wave, as indicated at 552. Block 552 may be performed by an extracardiac device (ED) or by an LCP in various different examples, and the P-wave may be sensed using an electrical waveform (electrocardiogram or cardiac electrogram), for example as in U.S. patent application Ser. No. 15/633,517, or by use of a mechanical sensor as in U.S. patent application Ser. Nos. 15/642,121, 15/625,655, 15/646,999, 15/654,393, 15/635, 921, and/or 15/630,677, the disclosures of which are incorporated herein by reference.

A pace output is generated at 554 by the LCP, and a sense and compare step 556 follows. The sensing may be of any of the signal types noted below in FIG. 18, and may be performed by the LCP or the ED. In several embodiments, the LCP performs sensing using an intracardiac sensor circuit or circuits for one or more of sound, pressure, impedance, motion, or optical changes, or, alternatively, using a sensed cardiac electrical signal. Comparison is performed relative to a template. The template is described at 558 as a preferred template, meaning that the template used in block 556 may be a template for the sensed signal representing a preferred pacing outcome, such as a fusion beat. The comparison step is preferably performed by the same device that performs the sensing, though in some examples, a sensed signal may be communicated out to a second device that stores the templates and performs comparisons.

If block 556 yields a match 560, the method iterates back to block 552, as the system can conclude based on template matching that the pace therapy successfully caused a desirable cardiac outcome. If instead there is no match, the method proceeds via block 570 to compare to one or more other templates at 572. Here the one or more "other" templates may correspond to identified outcomes generated at known offsets from an ideal pace timing. If block 572 yields no match, this suggests that neither the preferred outcome, nor identified alternative/offset outcomes have taken place, and re-initialization should be considered as indicated at 582.

For example, re-initialization may occur after a predetermined quantity of pacing therapies end up with no match at 580, such as if pacing fails to yield any matches for 1, 2, 5, 10, or up to 100, or more consecutive therapy cycles, or if a threshold quantity or percentage of therapy deliveries end at block 580 over a period of time. Re-initialization may comprise interrupting pace therapy delivery to observe one or more intrinsic cardiac cycles to develop new timing criteria for use in the device. Pace therapy is then delivered using the data from the intrinsic cardiac cycles and the template formation steps shown above relative to FIG. 14 may be performed again. Re-initialization may also include issuing an alert to the patient and/or a physician, such as by use of a home monitoring apparatus or a mobile device or programmer to communicate with the implanted system, suggesting that re-initialization be observed in-clinic or otherwise checked for validity.

For some examples, re-initialization may be performed after first making other adjustments, such as increasing a pacing therapy output amplitude and/or pulse width, to ensure that the failure to match expected CRT parameters is not a result of delivering too little energy with a pacing therapy output. For example, lack of capture due to inadequate pacing amplitude and/or pulsewidth may cause the resulting heart beat to mismatch applied parameters. Pace threshold measurement, such as a pace capture optimization, may be performed prior to re-initialization triggering, if desired.

For examples that obtain context information during template formation, a conclusion of no match 580 may trigger assessment of context 584 such as by determining whether context has changed with a new patient posture, activity level, time of day, or rate. In other examples, the preferred templates 558 and other templates used in block 572 may be updated using context 584 such as by selecting different templates in response to a change in patient posture, activity level, cardiac rate, or time of day, or other contextual information.

If there is a match at block 572, then the system takes a step to implement an offset in the P-sensing block 552 by artificially moving the "P-sense" forward or backward in time to adjust pace timing. One difficulty with such an approach is that it may not address uncertainty in P-wave sensing as well as an actual modification of P-wave sensing itself. Thus a method as in FIG. 16 may be used instead.

FIG. 16 shows another example. P-wave sensing is performed at block 602, with pacing delivery at 604, followed by sensing and comparison to a preferred outcome template 606. If a match 608 is found, the method returns to 602. If no match is found 610, comparisons are made to other templates at 612; if there is no match 626, either re-initialization 624 and/or context 628 may be considered. In these respects, the method of FIG. 16 is similar to that of FIG. 15.

However, if there is a match 614 to one of the "other" templates in the comparison at 612, an additional sequence occurs. The system reassesses the P-wave sensing data at 616. In particular, given the match to an offset template in block 612, the reassessment at 616 is performed to determine whether signal(s) analyzed to sense a P-wave include a "peak" or other indication that a P-wave may have occurred but was not identified. The aim in block 616 is to determine if there is a P-wave signal that could have been missed which would accord with the offset of the matching template.

For example, an offset template used in block 612 may correspond to delivering the pace therapy 20 milliseconds earlier than desired; if there is a P-wave peak about 20 milliseconds after the detected P-wave, then an adjustment can be made to one or more settings to ensure that the P-wave will be detected more accurately for a subsequent cardiac cycle. For example, in FIGS. 21-25, below, there are various illustrations of a P-wave signal, or a correlation signal generated from a P-wave signal, where multiple peaks, each possibly representing a P-wave, can be found. In addition, FIG. 26 shows certain illustrative adjustments that may be performed to enhance P-wave detection accuracy.

If the re-assessment 616 finds a P-wave at a time corresponding to the timing of the offset template match, this is treated as confirmation 618 of the offset template, and an adjustment 620 to P-wave sensing is made before returning to block 602. Such and adjustment 620 may be performed to accommodate the knowledge that current P-wave sensing method is not resulting in a preferred pace outcome. If the reassessment at 616 cannot confirm the offset, this is treated as a no match 622, and the method again looks at context 628 and/or re-initialization.

Figure 17:
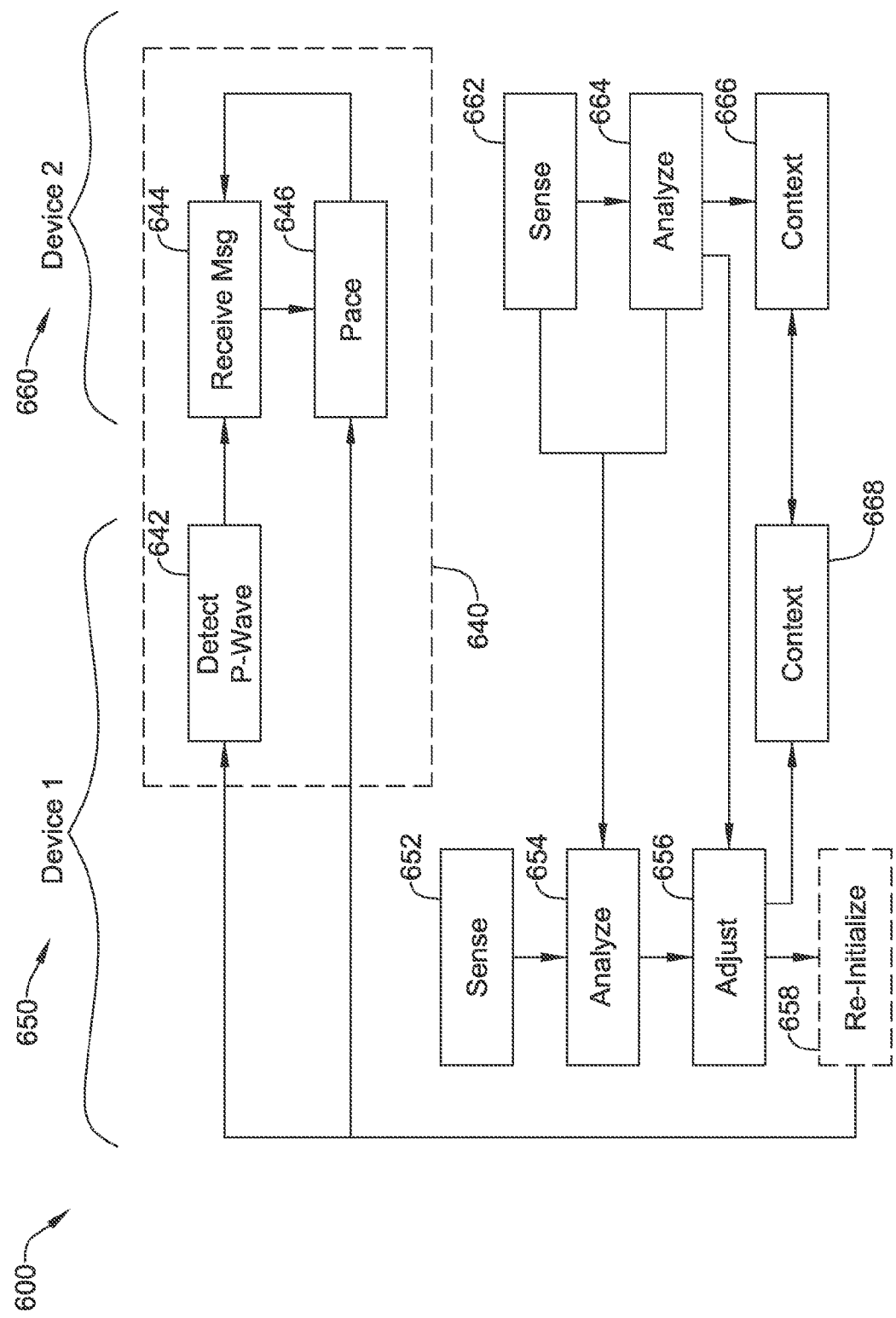
FIG. 17 shows an example allocating certain functions among a multi-device system.

FIG. 17 shows an example allocating certain functions among a multi-device system. A pacing protocol is followed in this example as shown at 640. A first device 650 detects the P-wave 642 and issues a message to a second device 660, which receives the message 644 and then delivers a pace output 646 using the received message. The pace protocol may be as in any of U.S. patent application Ser. Nos. 15/633,517, 15/684,366, and/or 15/710,118, the disclosures of which are incorporated herein by reference. For example, Device 1 650 may be an extracardiac device (ED) such as an SICD or SCM, and Device 2 may be an LCP. Device 1 650 may alternatively be an LCP or an intracardiac sensor device placed to capture atrial signals.

Meanwhile, one, the other, or both devices 650, 660 may be performing additional sensing and analysis to monitor pacing efficacy. For example, sensing 652, analysis 654, and adjustments 656 may be generated by Device 1 650 by the use of methods and other examples shown in U.S. patent application Ser. No. 15/684,264, titled CARDIAC RESYNCHRONIZATION USING FUSION PROMOTION FOR TIMING MANAGEMENT, the disclosure of which is incorporated herein by reference. In various examples, however, the LCP operating as Device 2 performs one or more of sensing 662, analysis 664, and observation of context 666, communicated back to Device 1 650 for generating adjustments 656. In some examples, Device 2 660 performs sensing 662 and communicates sensing outputs for analysis 652 in Device 1 650. In other examples, Device 2 performs sensing 662 and analysis 664 to determine template matching using context 664, while Device 1 performs further analysis 654 to observe P-wave sensing data and confirm an offset, as in block 616 in FIG. 16, above. Re-initialization 658 may be triggered by either device citing persistent system difficulty obtaining indicia of desirable pacing output.

Figure 18:
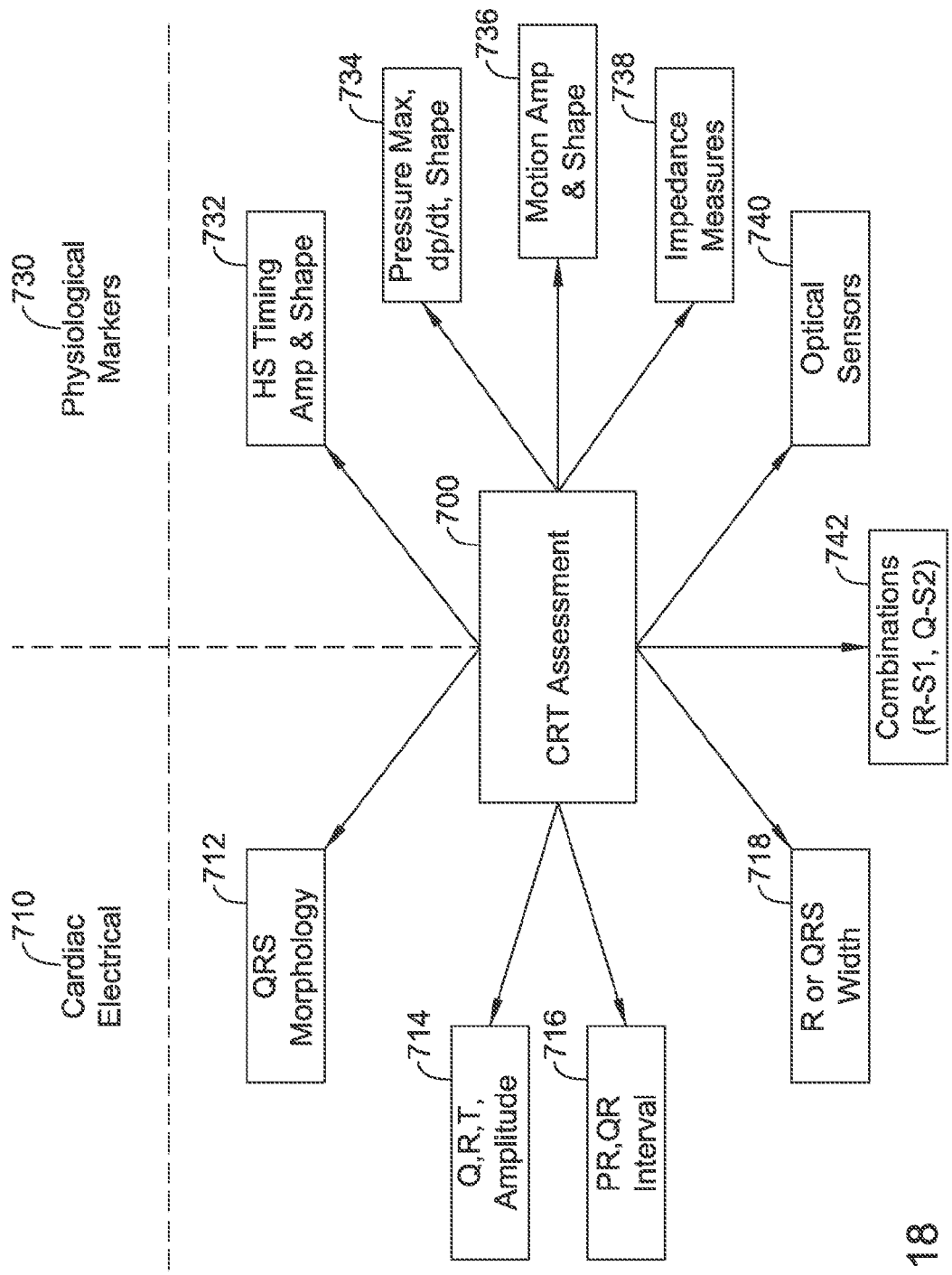
FIG. 18 illustrates a number of signal types useful in various examples.

FIG. 18 illustrates a number of signal types useful in various examples. The signals can be used to verify pacing efficacy and may range from cardiac electrical signals 710 to an array of physiological markers, as well as combinations thereof, any of which may be viewed as biological signals useful in providing and/or assessing CRT. For example, CRT assessment 700 may be performed by analyzing QRS morphology 712 using for example feature analysis (shape features such as turning points, area under a curve, etc.) and/or template matching. Additionally or alternatively, CRT assessment 700 may be performed by analyzing Q-wave, R-wave, and/or T-wave amplitude, or by relative comparison among different amplitudes, as indicated at 714. Additionally or alternatively, CRT assessment 700 may be performed by analyzing various intervals or segments of cardiac signal data such as by observing the PR interval, the QR interval, the ST interval, or other feature, as indicated at 716. Additionally or alternatively, CRT assessment 700 may include analysis of R-wave width and/or QRS width, as indicated at 718.

Physiological markers 730 may be used as well. For example, CRT assessment 700 may analyze heart sound timing, amplitude, and/or shape, as indicated at 732. Additionally or alternatively, CRT assessment 700 may include analysis of a pressure signal such as an intracardiac pressure, using for example, maximum or minimum pressure, slope of changes in pressure, a difference between minimum and maximum pressure, and/or shape. Additionally or alternatively, CRT assessment 700 may include analysis of a motion sensor output such as using a motion sensor attached to a portion of the heart as part of an LCP, or a motion sensor placed outside of the heart on an ED, and observing, for example, amplitude of the output signal, changes in the output signal, turning points in the output signal relative to time, and/or shape of the output signal of the sensor, as indicated at 736. Additionally or alternatively, CRT assessment 700 may include measurement of impedance 738 which may be determined as described in U.S. patent application Ser. Nos. 15/654,261, and 15/630,677, for example, the disclosures of which are incorporated herein by reference. Additionally or alternatively, CRT assessment 700 may include analysis of the output of one or more optical sensors, which may be used to generate cardiac timing features or pressure surrogates by, for example, observing reflected signals from blood flow; times of increased and decreased blood flow suggest various events in the cardiac cycle.

The various inputs for CRT assessment 700 can also be used in various combinations. For example, interval analysis can be useful to determine whether synchronization of cardiac contraction is occurring in a desirable manner. An interval from an R-wave onset or peak to the heart sound S1 is an example. Another example may be the interval from a Q-wave onset or peak to heart sound S2. Combinations may also take into account the timing of CRT pace delivery to various events. For example, the period from a pacing output to a motion signal indicating ventricular contraction, or to heart sound S1 indicating AV valve closure, may be observed.

In several embodiments, the LCP is configured to provide the inputs for CRT Assessment. For example, an LCP may be well placed to observe one or more of heart sounds 732, intracardiac pressure 734, motion 736, cardiac impedance 738, and/or optically observed blood flow 740. The LCP may also be used to detect one or more parts of the cardiac electrical signal 710. For example, an LCP may include a sensor for detecting one or the other of heart sounds and intracardiac pressure (the difference between a pressure signal and a sound signal being largely one of frequency), an accelerometer to obtain cardiac motion and/or overall motion indicating, for example, changes in patient posture or activity level, one or more optical sensors such as an optical device outputting an optical signal and determining reflectance thereof, and/or a sensor(s) to detect cardiac impedance as in U.S. patent application Ser. Nos. 15/654,261, and 15/630,677, for example, the disclosures of which are incorporated herein by reference. In a further embodiment, a motion signal may be used to determine cardiac contractility and to make adjustments as needed.

Alternatively, the ED, or both the ED and the LCP, may observe any of the noted features. For example, an ED with a lead implanted substernally (such as in US PG Patent Pub. No. 2017/0021159, titled SUBSTERNAL PLACEMENT OF A PACING OR DEFIBRILLATING ELECTRODE) and/or in the internal thoracic vein (such as in U.S. patent application Ser. No. 15/667,167, titled IMPLANTATION OF AN ACTIVE MEDICAL DEVICE USING THE INTERNAL THORACIC VASCULATURE), may be positioned to capture heart sounds and/or cardiac motion. A subcutaneous lead and/or canister may also detect heart sounds, or other features noted in FIG. 16. Placement of a lead in the internal thoracic vein and/or in an artery if desired may allow observation of blood flow characteristics and/or pressure. A lead crossing a portion of the thorax may be useful to observe transthoracic impedance and/or volume and changes thereof.

For example, a transthoracic impedance may be monitored as a measure of heart failure status; gradual changes over time may indicate that fluid is accumulating, suggesting that pace timing may need review. In an example, a method as shown in FIG. 15 may be used to establish a new offset of the overall timing algorithm in response to a change in fluid status. Changes may be monitored over a period of time by, for example, having the "change" limited in a manner such as shown below in FIG. 25, where the change is from a measurement from a prior time period, such as one to ten minutes prior to a current measurement. If the change exceeds a preset threshold (which may not be based on measurement but instead is set, if desired, by the physician or system in advance), it may be supposed that fluid is accumulating and an offset to either reduce or increase the pacing interval can be invoked. Continued monitoring may reveal whether the change had an impact; if so, the offset would be retained; if not, the offset may be reversed and a new offset, in the other direction this time, invoked.

In another example, an offset maybe introduced using a method as in FIG. 15 by monitoring for respiratory signals and making a change if a respiratory sinus arrhythmia is identified. Respiratory signals may be observed for example by detecting using an ED for muscle signals emanating near the diaphragm and/or by monitoring for transthoracic impedance changes and/or by observing motion signals related to diaphragm motion.

In some examples, multiple different cardiac electrical and/or physiological signals may be monitored in several layers. For example, a signal maybe monitored using a method as in FIG. 15 to induce offsets of a few milliseconds one way or another to attempt to maintain a desired CRT result, meanwhile, a method as shown in FIG. 16 may be used as well to monitor for errors in P-wave sensing.

Figure 19:
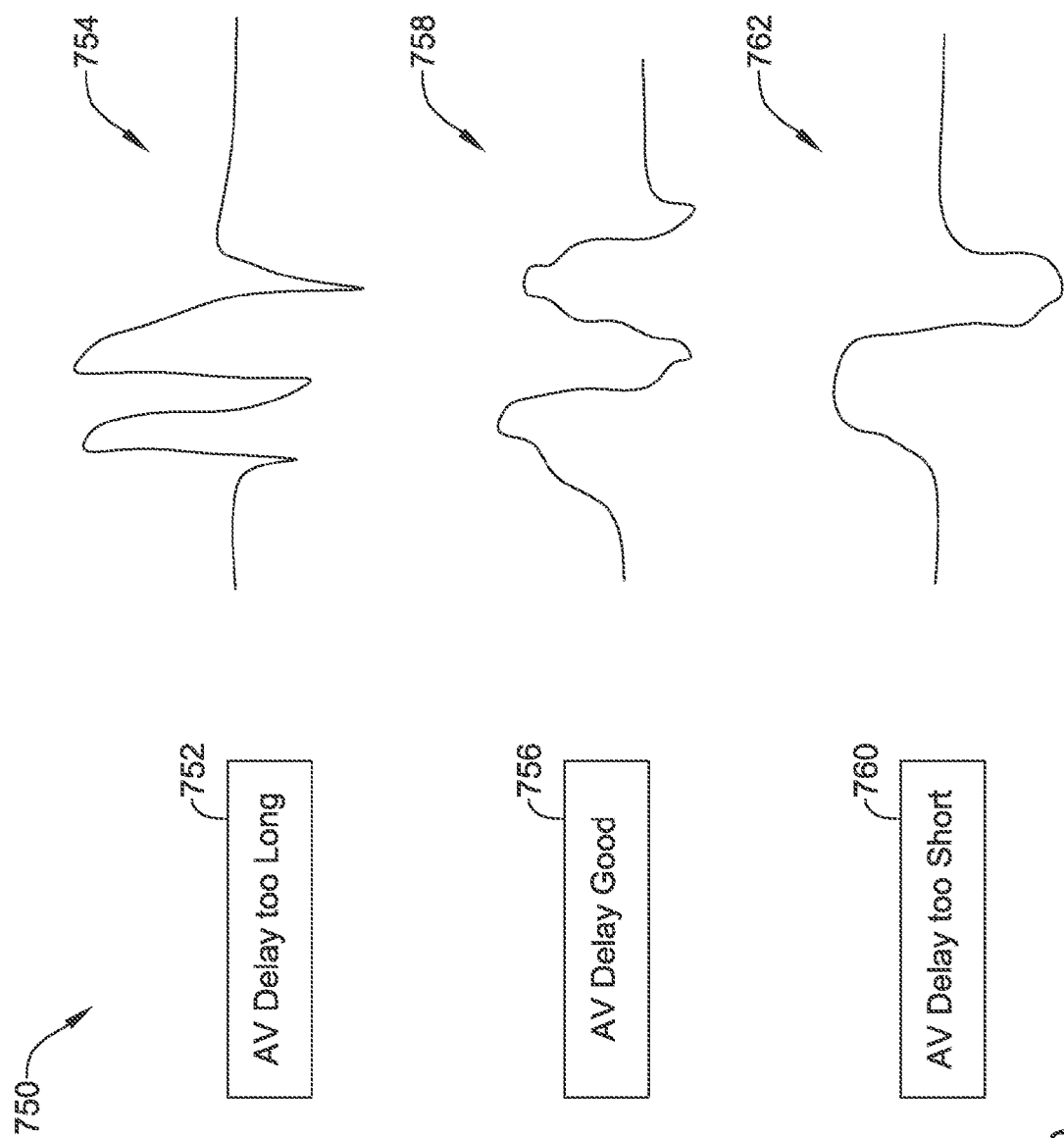
FIGS. 19-20 illustrate physiological signal templates for illustrative examples.
Figure 20:
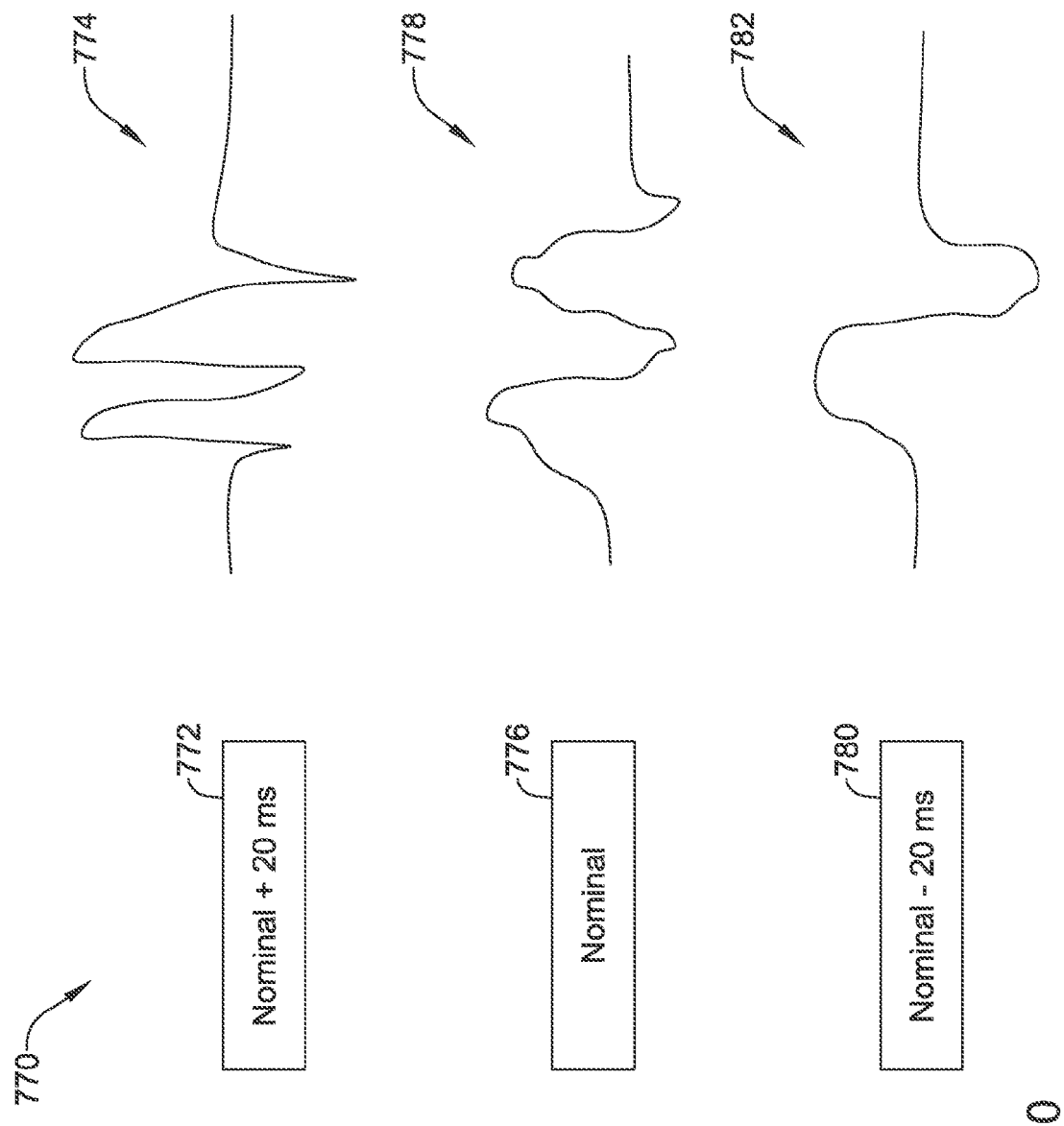

FIGS. 19-20 illustrate physiological signal templates for illustrative examples. For these examples, a heart sound has been selected as a demonstration exhibit. Other features may be used in like fashion, such as a template of the pressure waveform, a different heart sound, a template of cardiac motion from an accelerometer, a captured cardiac electrogram template from an LCP or a captured electrocardiogram from an extracardiac device, an optical interrogation/reflectance waveform representing the intensity of reflected light relative to time during a portion or all of the cardiac cycle, or other waveforms/signals noted above.

Referring to FIG. 19, three separate templates are shown at 750. In a first example, as indicated at 752, the AV Delay is too long, that is, the period from the actual atrial activation to a pace therapy delivery is longer than desired, such that resultant cardiac contraction resembles a native beat rather than a fusion beat. In one example, an outcome template may be generated using a heart sound sensor. A heart sound, S1 (indicating AV valve closure) is captured, and has a specific shape as shown at 754. When AV Delay is within a desired range, as indicated at 756, the S1 signal provides a different template as shown at 758. Finally, when AV Delay is too short 760, the resulting cardiac contraction would resemble a paced beat for the heart failure patient and provides a still different template as indicated at 762.

In use, a tiered approach as shown above in FIGS. 15-16 may compare a captured heart sound following delivery of a pace therapy to the desired template 758 and, if there is a match, then it is concluded that pacing was delivered as desired; if no match takes place, the captured heart sound can then be compared to one, the other, or both of the other templates 754, 762. In an alternative approach, the captured heart sound may be compared to each of the templates 754, 758, 762 and the system concludes that whichever best matches (preferably within or above a preset boundary of minimum degree of match) the captured heart sound is indicative of the quality of the pace therapy.

FIG. 20 is similar to FIG. 19. Three separate templates are shown at 770, this time characterized by the offset of each from nominal or desired pacing parameters. As indicated at 772, when a pacing pulse is delivered at an interval 20 milliseconds longer than nominal P-wave to Pace delay, a first template is captured as shown at 774. When pacing is delivered at the nominal delay, as indicated at 776, a second "desired" template is formed as shown at 778. Finally, when pacing is delivered at an interval that is 20 milliseconds less than the nominal P-wave to Pace delay, as indicated at 780, a third template is captured as shown at 782. The "Nominal" delay may be in the range of 100 milliseconds, for example, though the nominal setting may vary by patient or due to other factors such as specifics of system design.

In an alternative example, rather than using a set time period as the basis for defining separate templates, a system approach may be to first form the nominal template. Next, the AV delay can be adjusted in small increments to capture new signals for comparison to the nominal template 778, until a "no match" threshold is crossed—that is, until the newly captured signal no longer matches the nominal within predetermined bounds. Then a new template may be formed at the offset from nominal (or at a larger offset up to, for example, twice the offset that generates the no-match signal) used to obtain the non-matching signal. The process may be repeated to generate a template on either side (both longer and shorter) than the nominal setting. Such a process may be used to generate templates as characterized in FIG. 19, for example.

Figure 21:
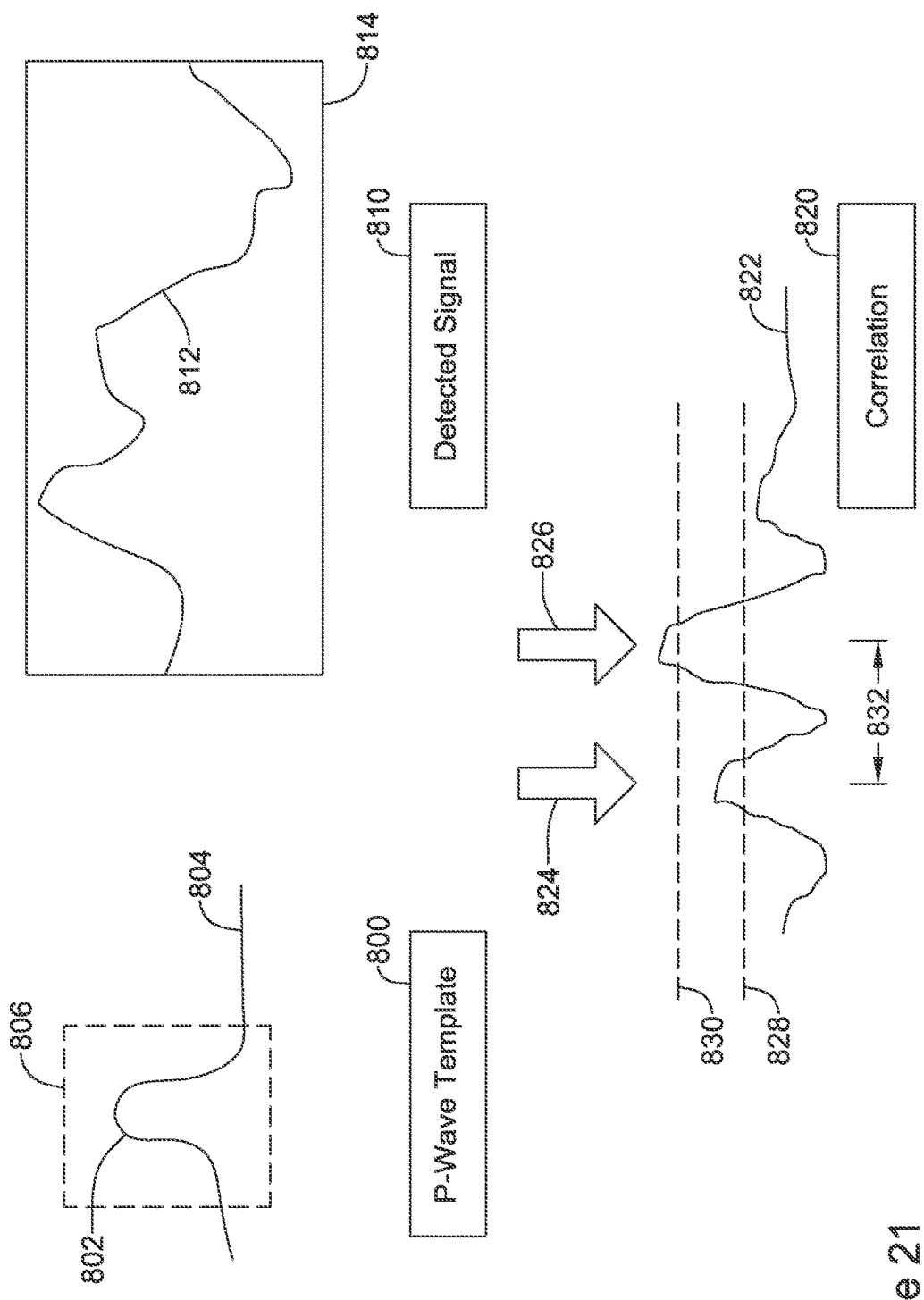
FIGS. 21-23 show examples of P-wave detection methods and issues that can arise in each leading to misdetection of the P-wave.
Figure 22:
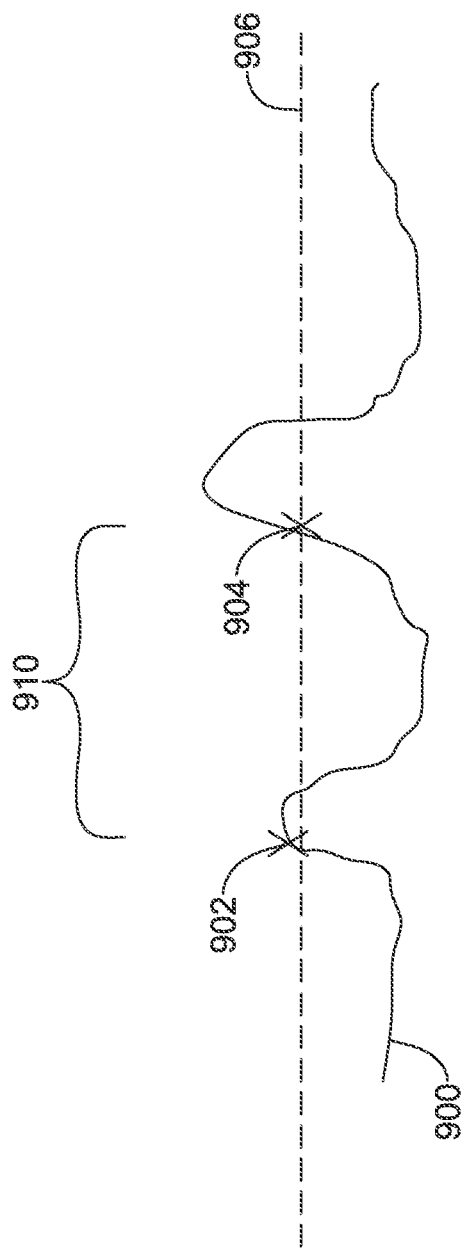
Figure 23:
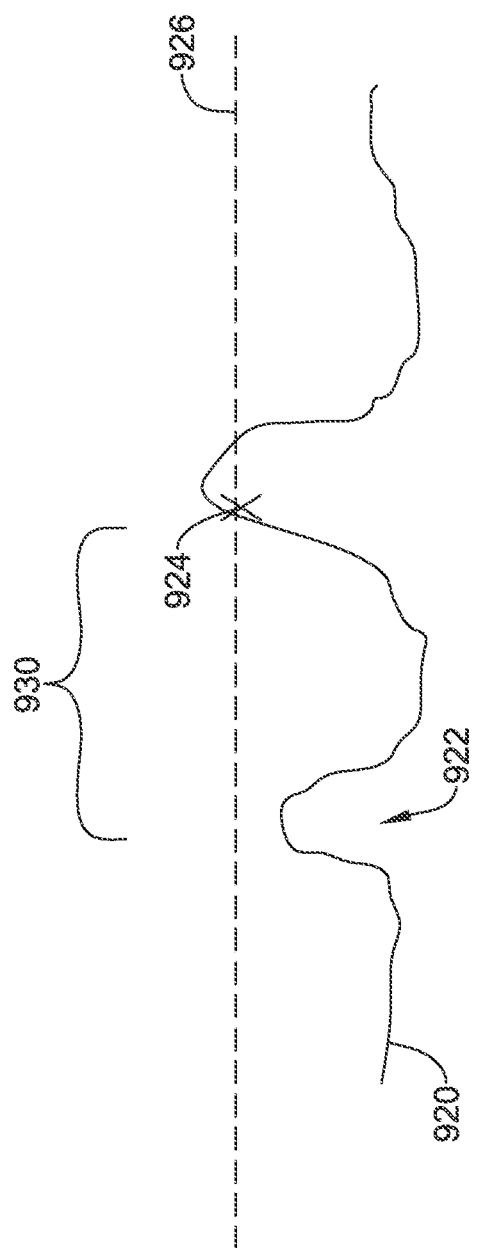

FIGS. 21-23 show examples of P-wave detection methods and issues that can arise in each leading to misdetection of the P-wave. Referring first to FIG. 21, a P-wave template 800 is established by finding a P-wave peak 802 in a trace 804, and establishing a window 806 for the template comprising a segment of the trace/signal 804 including the peak 802. In order to identify a P-wave in a detected signal 810, a window for the signal 812 is defined at 814. The template 800 is then repeatedly compared using correlation or difference of area, or other comparison technique, to portions of the signal 812 to yield a series of comparisons. In FIG. 21 the analysis result is shown as correlation 820, mapped at 822 for illustrative purposes. Peaks 824 and 826 represent points in time where the detected signal 810 was relatively more similar to the template 800 than at other points in time. To identify the P-wave, then, one of the peaks 824 may be selected. The first in time peak 824 may be selected or the largest peak 826 may be selected, for example. A match threshold may be set instead, if desired, as shown at 828 and/or 830, for example.

For illustrative purposes, an interval 832 between the correlation peaks 824, 826. In the above examples where an offset template matches a detected response signal, this interval 832 may be used to determine whether there is an alternative P-wave detection available to the system. For example, if the system were to identify peak 824 as the P-wave and pace using peak 824 as a timing reference or fiducial, and if analysis as shown above in FIG. 16 is performed and the desired template fails to match, then offset templates would be considered. If an offset template matches a captured signal, the P-wave re-assessment would analyze where a non-selected P-wave peak, such as peak 826, occurs at a point in time corresponding to the offset of the offset template that matches. To be more particular, assuming an offset template matches a captured signal (block 614 in FIG. 16), and the offset corresponds to pace delivery at an AV delay 20 milliseconds shorter than nominal, then if peak 824 was identified as the P-wave, the system would respond by making an adjustment to select peak 826 instead, such as by shifting from using a match threshold 828 to match threshold 830.

Rather than shifting the template through the entire incoming signal, the incoming signal may be analyzed to identify peaks in the signal and comparing the template to the peaks, reducing the number of calculations. In such an approach, a match may be declared if the correlation exceeds a match threshold.

FIGS. 22-23 show an alternative to FIG. 21. Referring to FIG. 22, the cardiac electrical signal is shown at 900, with possible P-wave peaks at 902 and again at 904. If a detection threshold as shown at 906 is used, then the system will detect peak 902 as a P-wave, assuming the first peak to cross the threshold 906 is deemed the P-wave. For subsequent analysis purposes (such as a reassessment in block 616 in FIG. 16), the data may be stored to show that another peak appears and relates to another threshold crossing at 904, with an interval between the threshold crossings as shown at 910. The interval 910 may be used to confirm whether there is a possible P-wave in the signal 900 at an interval corresponding to a matching offset template, should there be one.

FIG. 23 is similar to FIG. 22, with the signal at 920 and peaks at 922, 924. Here, the detection threshold 926 passes over the first peak 922 but not the second 924. Again, interval 930 may be tracked for use in reassessment (such as reassessment in block 616 of FIG. 16).

Figure 24:
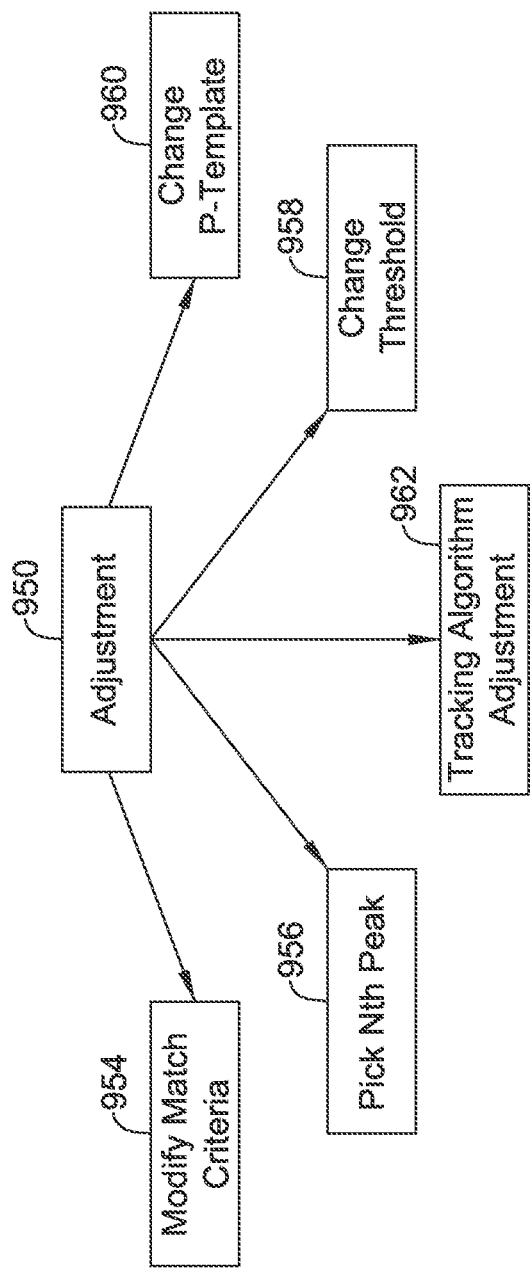
FIG. 24 shows a number of different adjustments to P-wave detection methods that may be used.

FIG. 24 shows a number of adjustments that may be made in response to a determination that P-wave sensing has encountered a difficulty. Adjustments may be used in block 620 of FIG. 16, for example. The adjustments 950 as shown as including, for example, modifying match criteria 954. Such an adjustment may be performed to accommodate the knowledge that the current P-wave sensing method is not resulting in a preferred pace outcome. Here, for example, a match threshold used to determine whether a P-wave template matches an incoming signal, such as shown in FIG. 21 with thresholds 828, 830.

Another adjustment 950 may comprise picking an "Nth" peak 956 or changing which of a set of peaks are to be identified as the P-wave. That is, a system may be set up to detect peaks in the cardiac electrical signal in a P-wave window, such as signal peaks exceeding a set threshold (a preset amplitude for example) or a variable threshold (a multiple of the RMS voltage of the incoming signal, or a fraction of an R-wave detection threshold). The $1^{st}$ such peak may be selected or, if desired or adjusted to do so, a $2^{nd}$, $3^{rd}$ or other "Nth" peak may be selected.

Another adjustment 950 may comprise changing a P-wave detection threshold 958 to raise or lower the required amplitude. A fixed threshold as shown in FIGS. 22-23 may be used, or the threshold may vary such as by setting a P-wave detection threshold as a fraction of an R-wave detection threshold. The adjustment in block 958 may include modifying the percentage used, or the absolute amplitude, or other parameter as desired.

Another adjustment 950 may comprise changing the P-wave template 960. For example, a system may store multiple P-wave templates for use in different contexts (as noted above in FIGS. 14-16, for example). A change in context, or identification of P-wave sensing difficulty, can be used to prompt selection of a different P-wave template. The change in template may comprise changing the window of signal used for a template to expand the window or narrow the window.

Match criteria, thresholds and templates may be applied to P-wave indicia. As used herein, P-wave indicia may be, for example, a detected cardiac electrical signal, across an entire cardiac cycle or in a window selected to focus on the likely time of the P-wave. P-wave indicia may instead be a series of correlation results calculated over time as a P-wave template is compared to a sensed cardiac electrical signal, either over a large portion of the cardiac cycle or across a window selected to encompass P-wave occurrence. Thus P-wave indicia may be direct representations of the electrical P-wave, or may be a secondary function developed from the electrical signal.

Another adjustment 950 may comprise making a change to a tracking method 962. For example, U.S. Pat. No. 8,332,034, the disclosure of which is incorporated herein by reference, discusses the use of heart sounds in assessing the mechanical action of a subject's heart, and discloses a heart sound recognition circuit that is configured to recognize heart sounds in a reliable and consistent manner. For example, in the U.S. Pat. No. 8,332,034 patent, a heart sound may be identified by tracking both the peak energy as well as a previously detected heart sound to establish the occurrence of the desired heart sound among several heart sound peaks. To apply this concept to the P-wave detection, a dynamic tracking method detects the most consistent and largest—or otherwise selected—peak in the underlying P-wave indicia. For example, a dynamic tracking method adapted from U.S. Pat. No. 8,332,034 can be used by initially identifying a P-wave using a first rule, such as maximum peak amplitude. As additional cardiac cycle data is captured, and as feedback from a pacing analysis method as shown above is captured, adjustments can be made to better select a peak occurring within a selected window, or with selected rules being met. A Viterbi method approach may be taken by initially selecting a peak from a plurality of available peaks in a P-wave indicia, and applying dynamic tracking to repeatedly obtain the same peak. Using such a dynamic tracking method, the goal is not necessarily to get the exact "P-wave", but instead to attain a P-wave detection outcome that allows for reliable CRT timing.

An adjustment 950 may be made by flagging an incorrect outcome and restarting the analysis for dynamic tracking 962 using a "more correct" peak in the P-wave indicia, and tracking to the newly selected peak. Dynamic tracking 962 may include setting, during initialization (referring briefly to FIG. 13) using fiducials 432, a window 434, specific set features 436, and/or a template 438, as by selecting a fiducial (a threshold crossing, inflection point, turning point, etc.) based on a feature (such as a rising edge) generated by comparing a template to a received signal within a window, for example. Adjustment to the dynamic tracking 962 may further specify one or more of the fiducial, window, feature, and/or template, such as by observing a peak rather than an inflection point, or observing an N+1 peak rather than an Nth peak. Thus the adjustment may be to select a different feature of the same type (selecting a different peak amongst a set of peaks), or by selecting a different feature type entirely (an inflection point rather than a peak, for example).

Figure 25:
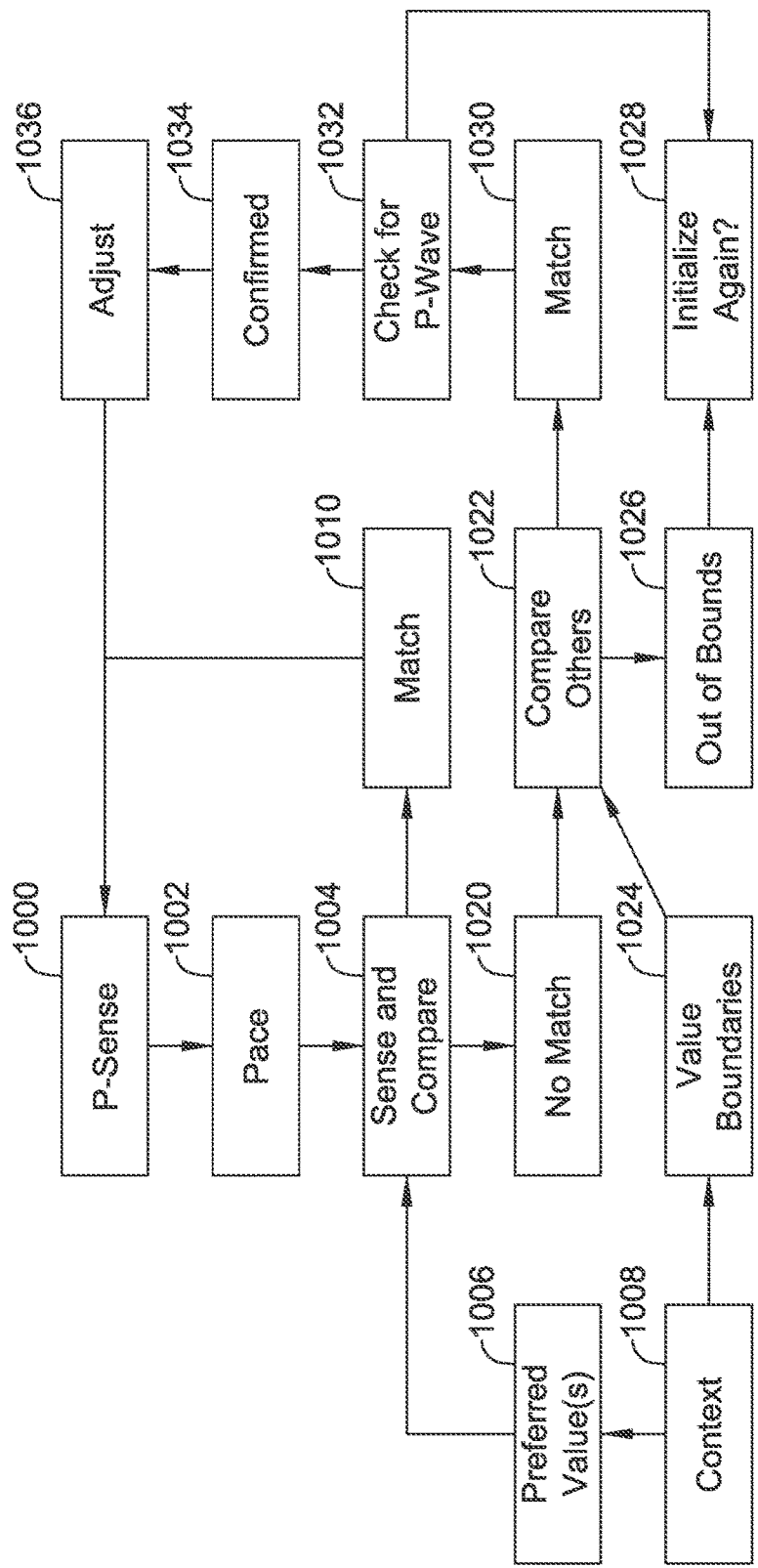
FIG. 25 illustrates a method of monitoring an enhancing P-wave detection using value boundaries rather than templates.

FIG. 25 shows an example using value boundaries rather than templates. In this example, a P-wave is sensed at block 1000 and used in one form or another to assist with managing a pace delivery 1002. A signal, such as one of the signals in FIG. 18, above, is sensed and compared 1004 to one or more preferred values 1006. In this example, device context 1008 may be used to select the one or more preferred values 1006. If the sensed signal matches 1010 the preferred values 1006, the system returns to the P-sense block 1000 for a next iteration of the method.

If the sensed signal does not match 1020 when checked at block 1004, the system next compares the sensed signal to one or more other parameters, such as a set of value boundaries 1024. The value boundaries 1024 may be set similar to how the templates are formed above. For example, the value boundaries may be set by increasing the CRT pacing interval by a set amount and measuring a sensed signal parameter, and then decreasing the CRT pacing interval by a set amount and re-measuring the sensed signal parameter to obtain high and low boundaries for the sensed signal parameter. The sensed signal parameter may be, for example, an interval between two cardiac electrical events, between two mechanical events (heart sound, motion, pressure, optical parameter peak, for example) of the same or different types, or between a cardiac electrical event and a mechanical event, between two impedance events (such as a measured maximum or minimum impedance), or an impedance event and a mechanical or cardiac electrical event. The sensed parameter may instead be, for example, a motion or heart sound peak, minimum, change, or rate of change. The sensed parameter may comprise any other signal that indicates cardiac response to a CRT pacing therapy.

If the senses signal does not match or fall within the value boundaries 1024, it may be deemed out of bounds, as indicated at 1026. This may trigger evaluation of context 1008 if desired. Otherwise, the out of bounds 1026 result calls for the system to consider re-initializing itself, as indicated at 1028.

If, on the other hand, the sensed signal matches the value boundaries, this is deemed a match 1030. "Matching" in either of blocks 1010 and 1030 may include comparing to the actual previously measured value (or value based on an offset, referred to in the figure and elsewhere herein as a value boundary) plus or minus some margin, and/or a previously measured value (or value boundary) plus or minus a standard deviation or variance, or other statistical error margin (for example if several measurements of the sensed signal are made). In the event of a match at block 1030, the system may next check whether a P-wave has taken place at an offset time that matches an offset used when establishing a value boundary. For example, if the value boundary is based on pacing at a 30 millisecond offset relative to an ideal pace interval/timing, and there is a likely or possible P-wave identified from P-wave data (FIGS. 21-23) at a similar 30 millisecond offset from the detected P-wave, then this confirms, as indicated at 1034, an adjustment 1036 (FIG. 24) will be made prior to returning to the P-sense block 1000. If the check for P-wave block 1032 does not find a corresponding P-wave at a relevant offset, the method/device instead goes to block 1028, to consider re-initializing.

In any of the above examples, the monitoring of CRT pacing quality may be performed on a continuous basis for each pace delivered for CRT purposes. In some embodiments, checking on CRT pacing quality may be performed less frequently, such as after a predetermined number of therapy deliveries have occurred, or at a predetermined interval. For example, every fifth to one-hundredth pace delivery may be checked, or CRT pacing quality may be checked once or more for each five seconds to two minutes of therapy. Other quantities and intervals may be used. In some examples, pacing therapy quality may be checked in response to a change of context such as when the patient's heart rate increases or decreases, or when the patient changes posture or activity level, for example, instead of or in addition to periodic checks.

A series of illustrative and non-limiting examples follows. These examples are provided for further illumination and is should be understood that other embodiments using other combinations of features are also contemplated.

A first illustrative non-limiting example takes the form of an implantable medical device (IMD) system comprising: a leadless cardiac pacemaker (LCP) having a plurality of LCP electrodes (FIG. 1, items 14, 40, FIG. 3), including: pacing means configured to issue cardiac pacing outputs via the plurality of LCP electrodes (FIG. 3, block 104 shows an LCP having a pulse generator module for generating an issuing cardiac pacing outputs via electrodes 118, 116, 120), LCP communication means configured to communicate to a second device (FIG. 3 shows a communication module 102 in an LCP), and LCP control means to control the pacing circuitry to generate cardiac resynchronization therapy (CRT) using data received with the communication circuitry (FIG. 3 shows a processing or control module 110 for controlling the pacing module 104 and communication module 102). Further in the first illustrative non-limiting example there is an extracardiac device (ED) comprising: a plurality of ED electrodes for receiving cardiac signals (the ED may be, for example and as described above, an implantable cardiac monitor or a second LCP device or, as shown in FIG. 1, a subcutaneous defibrillator 16, 18; the inclusion of such electrodes may include as identified in FIG. 1 electrodes on canister 16 and/or lead 18 at 24, 26 or lead branch 28; FIG. 2 shows an ED with electrodes such as an active housing 50, discrete electrodes 64, 66, and/or electrodes 72 on lead 70); ED communication means configured to communicate with at least the LCP communication circuitry (ED communication as shown in FIG. 2 may include a communication block 62 using an antenna 74 and/or operably connected via I/O block 58 to housing 50 and/or electrodes 64, 66 and/or 72, as described in associated text above); and ED sensing means for sensing cardiac signals from the plurality of ED electrodes and analyzing cardiac activity to identify cardiac cycles (sensing may be performed as explained above using the housing 50 and electrodes 64, 66, and/or 72, via I/O to processing block 52).

This first illustrative, non-limiting example, may be characterized by an improvement comprising: the LCP further including LCP sensing means to receive one or more biological signals and determine whether the CRT is achieving a desired result (such as electrical sensing module 106 and/or mechanical sensing module 108 shown in FIG. 3); the ED sensing means comprises P-wave sensing means to identify occurrence of a P-wave in a cardiac signal from the ED electrodes using a set of P-wave detection parameters (various examples of P-wave sensing by the ED are shown above including the use of dedicated circuitry and/or executable instructions for using, for example, a P-wave sensing window 316 to find P-wave 318 as shown in FIG. 10, and further illustrated graphically in FIGS. 11, 12, and 21-23; P-wave sensing is illustratively performed in blocks 552 (FIG. 15), 602 (FIG. 16), 642 (FIG. 17), and at 1000 in FIG. 25); the ED communication means is configured to communicate timing information related to outputs of the P-wave sensing means to the LCP to assist in the CRT (such communication is indicated in the linkage between blocks 642 and 644 in FIG. 17, for example); and wherein the ED and LCP are configured to cooperatively adjust the P-wave detection parameters in response to the LCP sensing means determines that the CRT is not achieving the desired result (such adjustment is indicated in the adjustment at blocks 576 (FIG. 15), 620 (FIG. 16), 656 (FIG. 17, which particularly illustrates the LCP and ED cooperating), and 1036 (FIG. 25); moreover, illustrative adjustments are shown graphically at FIGS. 21-23, and an overarching set of adjustments are noted in FIG. 24).

A second illustrative, non-limiting example takes the form of an IMD system as in the first illustrative non-limiting example, wherein the ED and LCP are configured to cooperatively adjust the P-wave detection parameters by: at a first time including at least a first cardiac cycle: the P-wave sensing means identifying occurrence of a P-wave using first P-wave detection parameters and the ED communication means communicating to the LCP first timing information related to the identified P-wave; the LCP control means using the first timing information to cause the pacing means to deliver one or more CRT pacing therapies; the LCP sensing means determining that a delivered CRT pacing therapy has failed to achieve the desired result; the LCP communication means communicating the failure to achieve the desired result to the ED; and in response to the LCP communicating failure to achieve the desired result, the P-wave sensing means adjusting the P-wave detection parameters to second P-wave detection parameters; at a second time following the first time, the second time including at least a second cardiac cycle: the P-wave sensing means identifying occurrence of a P-wave using the second P-wave detection parameters and the ED communication means communicating to the LCP second timing information related to the identified P-wave; and the LCP control means using the second timing information to cause the pacing means to deliver one or more CRT pacing therapies. This approach is shown in each of the methods illustrated in FIGS. 15-17 and 25, where adjustments are made in response to failure to match a preferred outcome template (see no match at 570 (FIG. 15), 626 (FIG. 16), and 1020 (FIG. 25) and/or the descriptions relative to the sense blocks 652, 662 and analysis blocks 654, 664 in FIG. 17). When the respective methods iterate, this defines a second time period for each such example.

Additionally or alternatively, the P-wave sensing means is configured to detect a P-wave by comparison of a cardiac electrical signal to a template to identify a match to the template, further wherein the P-wave sensing means is configured to adjust the P-wave detection parameters by adjusting a match criteria (FIG. 24, block 954).

Additionally or alternatively, the P-wave sensing means is configured to detect a P-wave by comparison of a cardiac electrical signal to a template to identify a match to the template, further wherein the P-wave sensing means is configured to adjust the P-wave detection parameters by changing the template (FIG. 24, block 960).

Additionally or alternatively, the P-wave sensing means is configured to detect a P-wave by identifying a peak among a set of peaks in a set of P-wave indicia; further wherein the P-wave sensing means is configured to adjust the P-wave detection parameters by storing a parameter for selecting an Nth peak of the set of peaks (FIG. 24, block 956).

Additionally or alternatively the P-wave sensing means is configured to detect a P-wave by comparing a set of P-wave indicia to a P-wave detection threshold; further wherein the P-wave sensing means is configured to adjust the P-wave detection parameters by adjusting the P-wave detection threshold (FIG. 24, block 958).

Additionally or alternatively the P-wave indicia comprise a series of samples of cardiac electrical data, as illustrated by the example of FIG. 11. Additionally or alternatively the P-wave indicia comprise a series of correlation results generated by the P-wave sensing means comparing a P-wave template to a cardiac electrical signal at a series of points in time, as illustrated by the example of FIG. 12.

Additionally or alternatively the P-wave sensing means is configured to detect a P-wave using a tracking analysis to track P-wave detections among a set of P-wave data captured for a series of cardiac cycles; further wherein the P-wave sensing means is configured to adjust the P-wave detection parameters by adjusting the tracking analysis (FIG. 24, block 962).

Additionally or alternatively, the LCP sensing means comprises: physiological template means for storing one or more templates for a physiological signal, at least one of the templates representing the physiological signal corresponding to a preferred pace timing; and determining means to determine whether a test physiological signal captured in relation to a CRT pace therapy matches one of the physiological templates representing the physiological signal corresponding to the preferred pace timing. FIG. 18 shows a number of CRT assessments using physiological markers 730, including heart sounds 732, pressure signals 734, motion signals 736, impedance measures 738, optical sensors 740, and combinations of any of heart sounds, pressure, motion, impedance or optical markers with one another or with electrical signals as indicated at 742. Additionally or alternatively, the LCP sensing means may instead rely on cardiac electrical markers 710 such as QRS morphology 712, Q, R, or T-wave amplitude 714, intervals between Q, R, and/or T waves 716, width of various signals 718, and/or combinations with the physiological markers.

Additionally or alternatively the physiological template means are configured such that the one or more templates comprises at least one offset template each representing the physiological signal corresponding to a known offset from the preferred pace timing; and wherein the determining means is configured to determine whether the test physiological signal matches one of the at least one offset templates and, if so, then to use the LCP communication means to communicate to the ED that an offset template match has occurred. Offset template formation may be achieved using the methods illustrated in FIG. 14 by dedicated circuitry and/or stored executable instruction sets. Graphical illustrations of the various templates are provided as well at FIGS. 19-20.

Additionally or alternatively the P-wave sensing means comprises offset match means to determine, in response to the LCP communicating that an offset template match has occurred, whether a P-wave may have occurred at an offset relative to a detected P-wave, and, if so, to make an adjustment to P-wave detection criteria relying on the known offset. Such offset matching to criteria is indicated in the comparison at blocks 572 (FIG. 15), 612 (FIG. 16), and 1022 (FIG. 25).

Additionally or alternatively, the P-wave sensing means comprises offset detection means configured, in response to the LCP communicating that an offset template match has occurred, to reanalyze the cardiac signal to determine whether one or more adjustments to a P-wave detection criteria would result in detection of a P-wave correlated to the known offset. Such verification is indicated by blocks 616/618 (FIG. 16), and 1032/1034 (FIG. 25).

Additionally or alternatively, the P-wave sensing means comprises offset adjustment means configured, in response to the LCP communicating that an offset template match has occurred, to make an adjustment to P-wave detection criteria using the offset. FIG. 15 shows an example in which the new offset is generated at block 578 based on matching to an offset criteria.

Additionally or alternatively, the determining means is configured to determine whether the test physiological signal fails to match any of the one or more templates and, if so, to use the LCP communication means to communicate that no template match occurred, and the ED further comprises re-initialization means configured to determine, based on whether the LCP communicates that no template match occurred, whether to perform a re-initialization of one or more ED and/or LCP system settings used in the P-wave sensing means and/or LCP. Such no-match conditions and associated assessment of re-initialization are indicated in FIG. 15 at blocks 580, 582, FIG. 16 at blocks 626, 624, and FIG. 25 at blocks 1026, 1028.

The various mean indicated may be embodied in dedicated circuitry such as dedicated blocks of logic circuitry, application specific integrated circuits, and combinations of digital logic and analog measurement or control features, as well as in executable instruction sets stored as firmware or software, as well as in other manners recognizable by the skilled artisan from the above description.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device (IMD) system comprising:
   a leadless cardiac pacemaker (LCP) having a plurality of LCP electrodes, pacing circuitry configured to issue cardiac pacing outputs via the plurality of LCP electrodes, LCP communication circuitry configured to communicate to a second device, and operational circuitry configured to control the pacing circuitry to generate cardiac resynchronization therapy (CRT) using data received with the communication circuitry, the LCP further comprising a sensing input circuit to receive one or more biological signals to determine whether the CRT is achieving a desired result;
   an extracardiac device (ED) comprising:
      a plurality of electrodes for sensing cardiac signals;
      ED communication circuitry configured to communicate with at least the LCP communication circuitry; and
      ED operational circuitry configured to receive sensed cardiac signals from the plurality of electrodes and analyze cardiac activity;
   wherein the ED operational circuitry is configured to obtain a cardiac signal from the plurality of electrodes, identify occurrence of a P-wave in the cardiac signal using a set of P-wave detection parameters, and use the ED communication circuitry to communicate to the LCP timing information related to the identified P-wave to assist in the CRT, such that the ED serves as a second device for purposes of the LCP communication circuitry; and
   wherein the ED and LCP are configured to cooperatively adjust the P-wave detection parameters.

2. The IMD system of claim 1 wherein the ED and LCP are configured to cooperatively adjust the P-wave detection parameters by:
   at a first time including at least a first cardiac cycle:
      the ED detecting a P-wave using first P-wave detection parameters and using the ED communication circuitry to communicate to the LCP first timing information related to the detected P-wave;
      the LCP using the first timing information to deliver one or more CRT pacing therapies;
      the LCP determining that a delivered CRT pacing therapy has failed to achieve the desired result; and
      the LCP communicating the failure to achieve the desired result to the ED;
   in response to the LCP communicating failure to achieve the desired result, the ED adjusting the P-wave detection parameters to second P-wave detection parameters;
   at a second time following the first time, the second time including at least a second cardiac cycle:
      the ED detecting a P-wave using second P-wave detection parameters and using the ED communication circuitry to communicate to the LCP second timing information related to the detected P-wave; and
      the LCP using the second timing information to deliver one or more CRT pacing therapies.

3. The IMD system of claim 2 wherein the ED is configured to detect a P-wave by comparison of a cardiac electrical signal to a template to identify a match to the template, further wherein the ED is configured to adjust the P-wave detection parameters by adjusting a match criteria.

4. The IMD system of claim 2 wherein the ED is configured to detect a P-wave by comparison of a cardiac electrical signal to a template to identify a match to the template, further wherein the ED is configured to adjust the P-wave detection parameters by changing the template.

5. The IMD system of claim 2 wherein the ED is configured to detect a P-wave by identifying a peak among a set of peaks in a set of P-wave indicia; further wherein the ED is configured to adjust the P-wave detection parameters by storing a parameter for selecting an Nth peak of the set of peaks.

6. The IMD system of claim 2 wherein the ED is configured to detect a P-wave by comparing a set of P-wave indicia to a P-wave detection threshold; further wherein the ED is configured to adjust the P-wave detection parameters by adjusting the P-wave detection threshold.

7. An IMD system as in claim 2 wherein the ED is configured to detect a P-wave using a tracking analysis to track P-wave detections among a set of P-wave data captured for a series of cardiac cycles; further wherein the ED is configured to adjust the P-wave detection parameters by adjusting the tracking analysis.

8. The IMD system of claim 1 wherein the LCP operational circuitry is configured to determine whether the CRT is achieving a desired result and to communicate to the ED operational circuitry to indicate whether the CRT is achieving the desired result, wherein the ED and LCP are configured to cooperatively adjust the P-wave detection parameters in response to the LCP determining that the CRT is not achieving the desired result.

9. The IMD system of claim 8 wherein the LCP is configured to determine whether the CRT is achieving a desired result by:
   storing one or more templates for a physiological signal sensed by the sensing input circuit, at least one of the templates representing the physiological signal corresponding to a preferred pace timing; and determining whether a test physiological signal captured in relation to a CRT pace therapy matches the template representing the physiological signal corresponding to the preferred pace timing.

10. The IMD system of claim 9 wherein:
the one or more templates comprises at least one offset template each representing the physiological signal corresponding to a known offset from the preferred pace timing; and
wherein the LCP is configured to determine whether the test physiological signal matches one of the at least one offset templates and, if so, to communicate to the ED that an offset template match has occurred.

11. The IMD system of claim 10 wherein the ED is configured, in response to the LCP communicating that an offset template match has occurred, to analyze the cardiac signal to determine whether a P-wave may have occurred at an offset relative to the detected P-wave, and, if so, making an adjustment to P-wave detection criteria.

12. The IMD system of claim 10 wherein the ED is configured, in response to the LCP communicating that an offset template match has occurred, to reanalyze the cardiac signal to determine whether one or more adjustments to a P-wave detection criteria would result in detection of a P-wave correlated to the offset of the offset template that matched the test physiological signal.

13. The IMD system of claim 10 wherein, in response to the LCP communicating that an offset template match has occurred, the ED is configured to make an adjustment to P-wave detection criteria using the offset.

14. The IMD system of claim 10 wherein, if the test physiological signal does not match any of the one or more templates, the LCP is configured to communicate that no template match occurred to the ED and further wherein, if the LCP finds at least a threshold quantity of test physiological signals fail to match any of the one or more templates, the IMD system is configured to perform a re-initialization of one or more CRT system settings.

15. An IMD system as in claim 1 wherein the LCP is configured to deliver CRT pacing output in response to communication of timing information related to the P-wave from the ED.

16. An IMD system as in claim 1 wherein the LCP is configured to deliver CRT pacing output according to a calculated interval relative to a prior CRT pacing output, and the LCP is configured to use the communication of timing information related to the P-wave to adjust the calculated interval.

17. An implantable medical device (IMD) system comprising:
a leadless cardiac pacemaker (LCP) for delivering cardiac resynchronization therapy (CRT), the LCP comprising:
a plurality of electrodes for delivering pacing therapy;
a sensing input circuit to receive one or more biological signals;
a pacing output circuit;
LCP communication circuitry; and
LCP operational circuitry configured to receive and analyze signals from the sensing input;
an extracardiac device (ED) comprising:
a plurality of electrodes for sensing cardiac signals;
ED communication circuitry configured to communicate with at least the LCP communication circuit; and
ED operational circuitry configured to receive sensed cardiac signals from the plurality of electrodes and analyze cardiac activity;
wherein the ED operational circuitry is configured to obtain a cardiac signal from the plurality of electrodes, identify occurrence of a P-wave in the cardiac signal, and use the ED communication circuitry to communicate to the LCP that the P-wave has been detected; and
wherein the LCP operational circuitry is configured to determine from its analysis of signals received from the sensing input whether the ED is incorrectly detecting the P-wave.

18. An IMD system as in claim 17 wherein the LCP is configured to deliver CRT pacing output in response to communication of timing information related to the P-wave from the ED.

19. An implantable medical device (IMD) system comprising:
a leadless cardiac pacemaker (LCP) for delivering cardiac resynchronization therapy (CRT), the LCP comprising:
a plurality of electrodes for delivering pacing therapy;
a sensing input circuit to receive one or more biological signals;
a pacing output circuit;
LCP communication circuitry; and
LCP operational circuitry configured to receive and analyze signals from the sensing input;
an extracardiac device (ED) comprising:
a plurality of electrodes for sensing cardiac signals;
ED communication circuitry configured to communicating with at least the LCP communication circuit; and
ED operational circuitry configured to receive sensed cardiac signals from the plurality of electrodes and analyze cardiac activity;
wherein the ED operational circuitry is configured to obtain a cardiac signal from the plurality of electrodes, identify occurrence of a P-wave in the cardiac signal, and use the ED communication circuitry to communicate to the LCP that the P-wave has been detected;
wherein the LCP operational circuitry is configured to use the pacing output circuit to deliver pace therapy and to use the sensing input circuit to determine whether a cardiac response to the pace therapy matches a desired metric; and
wherein the LCP operational circuitry is configured to communicate to the ED operational circuitry to indicate that the pace therapy does not match the desired metric.

20. An IMD system as in claim 19 wherein the LCP is configured to deliver CRT pacing output in response to communication of timing information related to the P-wave from the ED.

* * * * *